(12) United States Patent
Voellmy

(10) Patent No.: US 11,497,806 B2
(45) Date of Patent: *Nov. 15, 2022

(54) IMMUNIZATION AGENTS AND METHODS OF USE

(71) Applicant: HSF PHARMACEUTICALS SA, La Tour-de-Peilz (CH)

(72) Inventor: Richard Voellmy, La Tour-de-Peilz (CH)

(73) Assignee: HSF PHARMACEUTICALS SA, La Tour-de-Peilz (CH)

( * ) Notice: Subject to any disclaimer, the term of this patent is extended or adjusted under 35 U.S.C. 154(b) by 16 days.

This patent is subject to a terminal disclaimer.

(21) Appl. No.: 16/662,096

(22) Filed: Oct. 24, 2019

(65) Prior Publication Data

US 2020/0038501 A1    Feb. 6, 2020

Related U.S. Application Data

(63) Continuation of application No. 15/530,715, filed as application No. PCT/EP2015/069472 on Aug. 25, 2015, now Pat. No. 10,478,486.

(60) Provisional application No. 62/122,088, filed on Oct. 10, 2014, provisional application No. 62/070,443, filed on Aug. 26, 2014.

(51) Int. Cl.
  *A61K 39/245*    (2006.01)
  *A61K 39/12*    (2006.01)
  *A61K 39/00*    (2006.01)

(52) U.S. Cl.
  CPC ...... *A61K 39/12* (2013.01); *A61K 2039/5254* (2013.01); *C12N 2710/10334* (2013.01); *C12N 2710/10343* (2013.01); *C12N 2710/16034* (2013.01); *C12N 2710/16611* (2013.01); *C12N 2710/16634* (2013.01); *C12N 2710/16643* (2013.01); *C12N 2800/40* (2013.01); *C12N 2830/002* (2013.01)

(58) Field of Classification Search
  CPC ............. C12N 2830/00; C12N 15/86; C12N 2710/10332; C12N 2700/16611; A61P 31/22; A61K 39/245
  See application file for complete search history.

(56) References Cited

U.S. PATENT DOCUMENTS

| 7,906,312 B2 | 3/2011 | Voellmy |
| 8,137,947 B2 | 3/2012 | Voellmy |
| 2016/0008458 A1 | 1/2016 | Mahalingam et al. |

OTHER PUBLICATIONS

Vilaboa, N. et al. "Novel Gene Switches for Targeted and Timed Expression of Proteins of Interest" *Molecular Therapy*, Aug. 2005, pp. 290-298, vol. 12, No. 2.
Currier, M. A. et al. "Efficacy and Safety of the Oncolytic Herpes Simplex Virus rRp450 Alone and Combined With Cyclophosphamide" *Molecular Therapy*, 2008, pp. 879-885, vol. 16, No. 5.
Rice, S. A. et al. "Genetic Evidence for Two Distinct Transactivation Functions of the Herpes Simplex Virus α Protein ICP27" *Journal of Virology*, Apr. 1990, pp. 1704-1715, vol. 64, No. 4.
Markert, J. M. et al. "Conditionally replicating herpes simplex virus mutant, G207 for the treatment of malignant glioma: results of a phase I trial" *Gene Therapy*, 2000, pp. 867-874, vol. 7.

*Primary Examiner* — Bao Q Li
(74) *Attorney, Agent, or Firm* — Saliwanchik, Lloyd & Eisenschenk

(57) ABSTRACT

The present invention relates to a vaccine composition comprising an effective amount of a replication-competent controlled recombinant virus. Further encompassed are uses in immunization and methods of immunization employing compositions comprising a replication-competent controlled recombinant virus of the invention.

19 Claims, 6 Drawing Sheets
Specification includes a Sequence Listing.

IMMUNIZATION AGENTS AND METHODS OF USE

CROSS-REFERENCE TO RELATED APPLICATIONS

This application is a continuation of U.S. application Ser. No. 15/530,715, filed Feb. 21, 2017, which is the national stage of international application No. PCT/EP2015/069472, filed Aug. 25, 2015, which claims the benefit of U.S. Provisional Application Nos. 62/070,443, filed 26 Aug. 2014; and 62/122,088, filed 10 Oct. 2014, both of which are incorporated herein by reference in their entirety; including any drawings.

REFERENCE TO THE SEQUENCE LISTING

The present application is being filed along with a Sequence Listing in electronic format. The Sequence Listing is provided as a file entitled "VIR2A-PCT_ST25.txt", created 25 Aug. 2015, which is 4 KB in size. The information in the electronic format of the Sequence Listing is incorporated herein by reference in its entirety.

TECHNICAL FIELD

The present invention relates to certain replication-competent controlled viruses and their utilization for immunization.

BACKGROUND OF THE INVENTION

Vaccination is most probably the most cost-effective medical intervention that has saved countless human lives during its history of more than two hundred years. Among its most spectacular successes count the eradication of smallpox as well as the virtual disappearance of diphtheria, tetanus and paralytic poliomyelitis. Andre, F. E. (2003) Vaccinology: past achievements, present roadblocks and future promises. Vaccine 21: 593-5. In addition, vaccination has controlled, in at least part of the world, yellow fever, pertussis, *Haemophilus influenzae* type b, measles, mumps, rubella, typhoid and rabies. Still, important infections remain unpreventable as well as incapable of being treated by a therapeutic vaccine. Moreover, effectiveness of a number of vaccines is less than would be desirable. Clearly, the creation of new vaccines has not become routine, and development of immunization agents against certain diseases may require new approaches. The following examples illustrate some of the current challenges.

About 50% of ten-year-old American and European children are seropositive for herpes simplex virus HSV-1. Stanberry, L. R. Herpes simplex virus vaccines. In: Vaccines (Plotkin, S. A. et al., eds.) 5th edition. 2008. Saunders Elsevier. Prevalence increases to 70-80% in the sixth and seventh decades. Herpes simplex virus HSV-2 prevalence rises during adolescence and reaches peaks of 20% and 30% in Europe and the United States, respectively. Potentially life-threatening infection can occur in subjects with skin disorders. HSV infection of the eye may affect the conjunctiva, cornea or retina and can cause blindness. Perinatal herpes infection can include encephalitis or disseminated infection. Infection in immune-compromised subjects such as HIV patients may also be life-threatening. HSV infection has many complications, resulting in significant morbidity and mortality. It is noteworthy that acute genital herpes infection significantly increases the risk of HIV acquisition. HSV-1 and HSV-2 infections involve replication at the site of entry and spread of virus along nerve fibers to sensory ganglia where latency is established. The viruses can reactivate periodically/sporadically, migrate back to the periphery and replicate in the periphery. A number of prophylactic and therapeutic vaccine candidates were developed and tested clinically. Stanberry, L. R. (2008). At this time, no effective therapeutic or prophylactic vaccine is available. It has been argued that a successful therapeutic or prophylactic vaccine should elicit powerful antibody as well as T cell (Th-1) responses. Cunningham, A. L. and Mikloska, Z. (2001) The holy grail: immune control of human herpes simplex virus infection and disease. Herpes 8 (Supplement 1): 6A-10A.

It has been suggested that the goal of developing a prophylactic HSV-1 or HSV-2 vaccine may be too ambitious and that the focus should be on generating a therapeutic vaccine. In this regard, it is encouraging that a vaccine was able to be developed that shows effectiveness in preventing shingles (herpes zoster). Johnson, R. et al. (2007) Prevention of herpes zoster and its painful and debilitating consequences. Int. J. Infect. Dis. 11 (Supplement 2): S43-S48. The latter disease is caused by reactivation in sensory ganglia of varicella-zoster virus (VZV), another alphaherpes virus. The vaccine, made from the live attenuated Oka strain, is >60% effective in reducing the burden of illness or postherpetic neuralgia. This protection is associated with a boosted cell-mediated immune response. The Oka strain was also utilized to develop a highly effective, live attenuated vaccine for the prevention of chicken pox/varicella. Gershon, A. A. et al. Varicella vaccine. In: Vaccines (Plotkin, S. A. et al., eds.) 5th edition. 2008. Saunders Elsevier. Therefore, it can be argued that it should not be impossible to create effective herpes simplex vaccines. It is noted that development of an even more effective herpes zoster vaccine (or a varicella vaccine that cannot reactivate) would be a worthwhile goal.

Influenza is characterized typically by sudden fever, sore throat, cough, headache, myalgia, chills, anorexia and fatigue. Bridges, C. B. et al. Inactivated influenza vaccines. In: Vaccines (Plotkin, S. A. et al., eds.) 5th edition. 2008. Saunders Elsevier; Belshe, R. B. et al. Influenza vaccine-live. In: Vaccines (Plotkin, S. A. et al., eds.) 5th edition. 2008. Saunders Elsevier. Influenza is a high morbidity but relatively low mortality disease. Seasonal attack rates typically are between 5% and 20%. The death toll from complications of the illness is considerable. According to the WHO, the worldwide yearly death toll may lie between 250,000 and 500'000. Influenza viruses are enveloped and contain a segmented negative-sense RNA genome. The spherical viral particles have spikes consisting of hemagglutinin (HA) and neuraminidase (NA). HA is the major antigen against which the host antibody response is directed. Influenza A viruses are classified into subgroups based on the properties of their envelope proteins HA and NA. Sixteen H(A) and nine N(A) subtypes are currently known. Presently, influenza viruses of subtypes H1N1, H1N2 and H3N2 are circulating in humans. Influenza type A also infects birds including poultry, pigs, horses, dogs and even sea mammals. All known HA and NA subtypes could be isolated from wild aquatic birds, which constitute a natural reservoir and a source of genes for pandemic A-type viruses. Because of the error-prone mode of replication and selection in the host, influenza A and B viruses undergo gradual antigenic change in their two surface antigens, the HA and NA proteins. This phenomenon known as antigenic drift necessitates continuous vigilance and yearly review/update of strains used for vaccine production. Pandemics result from antigenic shift, i.e., introduction into the human population of a novel influenza A virus containing either only a novel HA subtype or both novel HA and NA subtypes.

Whole-virus inactivated influenza vaccines have been in use since 1945. Typically, vaccine viruses have been propagated in the allantoic cavities of embryonated hens' eggs. More recently, such vaccines also have been made from viruses amplified in mammalian cell lines. Since the 1970s, most inactivated vaccines are subvirus or split vaccines. Typical vaccines in use are trivalent, comprising HAs from H1N1 and H3N2 subtype influenza A strains and an influenza B strain (referred to as TIV). The variable efficacy of the inactivated virus vaccines (TIV), the short duration of protection, adverse reaction to parenteral administration (the primary route used) and the absence of induction of effective cellular immunity has led to the development of live attenuated influenza virus vaccines (LAIV). An intranasal vaccine was made based on temperature-sensitive and cold-adapted influenza virus A and B strains.

An updated systematic review and meta-analysis of vaccine efficacy and effectiveness data was published not long ago. Osterholm, M. T. et al. (2012) Efficacy and effectiveness of influenza vaccines: a systematic review and meta-analysis. Lancet Infect. Dis. 12: 36-44. The analysis focused on studies carried out in the United States and published between 1967 and 2011. Studies were selected based on a set of criteria that were intended to ensure scientific rigor and, to the extent possible, exclude bias. All criteria were fulfilled by 17 randomized, controlled trials showing vaccine efficacy (95% CI>0), of which trials 8 related to TIV and 9 to LAIV. The trials covered 24 influenza seasons and included almost 54,000 participants. Of the trials that revealed significant efficacy for TIV, 6 involved 18-64-year-old participants, one children aged 6-23 months and one included all age groups and reported a combined efficacy. The mean vaccine efficacy revealed by these trials was 62%. It is noted that none of the trials specifically tested vaccine effects in adults 65 years of age and older or in children aged 2-17. Of particular interest is a study on young children that was carried on over two seasons in both of which there was a good match between vaccine and circulating strains. Hoberman, A. et al. (2003) Effectiveness of inactivated influenza vaccine in preventing acute otitis media in young children: a randomized controlled trial. JAMA 290: 1608-16. Vaccine efficacy in the first season was 66% and in the second −7%. Regarding LAIV, mean efficacy from eight studies in children aged 6 months to 7 years was 78%. Osterholm, M. T. et al. (2012). Three studies on subjects aged 18-49 revealed no significant protection. One study in persons over 60 showed an overall efficacy of 42%, but efficacy in 60-69-year-olds seemed to be considerably lower than that in persons over 70. No qualifying study related to children aged 8-17 or adults between 50 and 59 years of age.

Nine of 14 observational studies that satisfied the inclusion criteria reported effectiveness of seasonal influenza vaccine. Osterholm, M. T. et al. (2012). These studies included 17 embedded or cohort analyses. Six of the 17 analyses (35%) showed significant effectiveness against medically attended, laboratory-confirmed influenza. In children of 6-59 months, significant vaccine effectiveness was found in 3 of 8 seasons (38%). One of two such studies reported vaccine effectiveness in subjects aged 65 and older. Based on these data it can be concluded that currently available influenza vaccines provide moderate protection against virologically confirmed disease, which protection is not long-lasting. No protection may be obtained in some seasons. Evidence for protection of the highest risk population, i.e., persons 65 years of age or over, is very thin indeed. More effective vaccines are clearly needed. Present vaccines rely largely on the induction of HA antibodies for protective effects. It has been proposed that future influenza vaccines should be capable of inducing potent (effector) T cell responses, i.e., should induce more complete immune responses. Osterhaus, A. et al. (2011) Towards universal influenza vaccines. Phil. Trans. R. Soc. B 366: 2766-73; Thomas, P. G. et al. (2006) Cell-mediated protection in influenza infection. Emerging Infectious Diseases 12: 48-54.

HIV/AIDS is a leading cause of death in Subsaharan Africa and an important cause of mortality worldwide. HIV are lentiviruses which are retroviruses that cause characteristically slow infections, producing disease after long latency periods in the presence of an activated host immune response. HIV includes HIV-1 and HIV-2, with HIV-1 being the more aggressive and more rapidly spreading virus. As a first step of the infection process, viral envelope protein gp120 binds to CD4 receptor and then to CCR-5 or CXCR-4 co-receptors on the surface of target cells. CD4 is present in T helper lymphocytes, monocytes-macrophages, follicular DC, Langerhans cells in the skin and microglia in the central nervous system.

At this time, there is no effective vaccine available against HIV/AIDS. A number of observations suggest that, in order to be effective, a vaccine must trigger a substantial cellular immune response. A number of vaccine candidates were tested in clinical trials. Recent pivotal trials made use of viral vectors to induce T-cell responses. To further increase efficacy, these trials also implemented prime-boost regimens. One such phase III trial used a combination of a priming canarypox virus expressing an HIV gp120 antigen and an HIV gp120 boost. Although a trend towards prevention of HIV-1 was found, the vaccine produced no beneficial effects on post-infection virus load or CD4+ cell counts. Draper, S. J. and Heeney, J. L. (2010) Viruses as vaccine vectors for infectious diseases and cancer. Nat. Rev. Microbiology 8: 62-73; Kim, J. H. et al. (2012) HIV vaccines—lessions learned and the way forward. Curr. Opin. HIV AIDS 5: 428-34. Another recent series of trials using replication-incompetent Ad5 expressing various HIV proteins as vaccines did not reveal any indication of efficacy. The latter experiences as well as the realization that a narrow CTL response can lead to the appearance of CTL escape mutants suggest that future vaccine candidates should be capable of inducing complete immune responses including broad CTL responses. Goulder, P. J. R. and Watkins, D. I. (2004) HIV and SIV CTL escape: implications for vaccine design. Nat. Rev. Immunol. 4: 630-40; Barouch, D. H. et al. (2002) Eventual AIDS vaccine failure in a rhesus monkey by viral escape from cytotoxic lymphocytes. Nature 415: 335-9.

Tuberculosis is caused by *Mycobacterium tuberculosis*. Smith, K. C. et al. (2008) Tuberculosis vaccines. In: Vaccines (Plotkin, S. A. et al., eds.) 5th edition. 2008. Saunders Elsevier. The disease represents a huge public health problem with approximately one third of the word population infected with the organism, despite widespread vaccination programs. Latent tuberculosis infection is the preclinical state of the disease. Outbreak of disease can occur within weeks or decades from the time of establishment of latent infection. Yearly deaths from tuberculosis range in the millions. The exact immunological mechanisms that underlie human resistance to *M. tuberculosis* remain to be elucidated. However, it is known that progressive disease is associated with a Th2 or a mixed Th1/Th2 response, whereas a pure Th1 response correlates with protection. Surcel, H-M. et al. (1994) Th1/Th2 profiles in tuberculosis, based on the proliferation and cytokine response of blood lymphocytes to mycobacterial antigens. Immunology 81: 171-6; Schauf, V. et al. (1993) Cytokine gene activation and modified responsiveness to interleukin-2 in the blood of tuberculosis patients. J. Infect. Dis. 168: 1056-9. The Bacille Calmette-Guérin (BCG) vaccines are the oldest vaccines currently in use. Unfortunately, the question whether the vaccines work has not been answered definitively. Efficacies between 0 and 80% have been reported. The exact immune response elicited by BCG vaccination as well as the mechanism of action within the host are not well understood. Smith, K. C. et al. (2008). Animal studies have been infrequent. Smith, D. W. (1985) Protective effect of BCG in experimental tuberculosis. Adv. Tuberc. Res. 22: 1-97. Nevertheless, the available information indicates that protective effects can be transferred with CD4 T-cells, but not with serum. Furthermore, the T-cell response is faster in vaccinated animals, resulting in more rapid macrophage activation.

New and more effective vaccines are clearly needed. The present invention relates to vaccine compositions comprising a replication-competent controlled virus as well as to methods of immunization utilizing the latter compositions.

Replication-competent viruses and virus pairs controlled by a SafeSwitch or a SafeSwitch-like gene switch were disclosed generally in U.S. Pat. Nos. 7,906,312 and 8,137,947.

SUMMARY OF THE INVENTION

In one embodiment the present invention provides an improved vaccine comprising a composition comprising an effective amount of a replication-competent controlled herpesvirus. The improved vaccine induces superior protective immunity in a mammalian challenge model when compared with a comparison vaccine comprising an equivalent amount of an attenuated herpesvirus that is replication-defective, provided that the attenuated herpesvirus and the replication-competent controlled herpesvirus have been derived from the same wild type virus. The latter wild type virus is also the challenge virus in the mammalian challenge model, i.e., the protective immunity assessed is that directed to this wild type virus. It is noted that improvement is established utilizing a relevant mammalian challenge model as human data are not yet available. A suitable mammalian challenge model is one in which infection of animals of the chosen mammalian species with the wild type virus of interest reproducibly results in a manifestation in the animals of a relevant aspect of the disease or condition induced in a human host by infection with the same or a similar wild type virus. When available, small mammalian animal models are preferred, and mouse models are most preferred. "Protective immunity" is understood as an immune response that prevents or mitigates/reduces the severity or duration of the latter manifestation of an aspect of the disease or condition that is induced by inoculation with wild type virus, or reduces mortality resulting therefrom.

The replication-competent controlled herpesvirus of the invention has the following set of properties:
(1) upon administration to a body region of a mammalian subject, the replication-competent controlled virus remains essentially non-replicating in the body region in the absence of activation or, alternatively (i.e., in a different embodiment), replicates with a similarly low efficiency as a replication-defective comparison virus administered to a similar subject in a similar composition, in a similar amount and to a similar body region as the replication-competent controlled virus, (2) exposure of the body region to a localized activation treatment activates the replication-competent controlled virus to undergo a round of replication in the body region, and
(3) upon activation, the replication-competent controlled virus replicates with an efficiency that is sufficient to induce in the mammalian subject an immune response that is more effective in reducing infection by the wild type virus from which the replication-competent controlled virus was derived and/or in reducing disease severity, disease duration or mortality subsequent to infection with said wild type virus than the immune response induced in a similar subject by a replication-defective comparison virus (replication-competent controlled virus and replication-defective comparison virus being administered in similar compositions, in similar amounts and to similar body regions of similar subjects).

The replication-defective comparison virus is a virus that has been derived from the same wild type virus as the replication-competent controlled recombinant herpesvirus for which it is to serve as a comparison. Such a replication-defective comparison virus will be disabled in at least one of the genes that are subjected to deliberate regulation in the replication-competent controlled virus. Disabled refers to the result of a manipulation or event that renders the gene incapable of expressing a functional gene product. A wild type virus is a virus that has been isolated from a subject or the environment and, although propagated in vitro or in animals, has not been subjected to any deliberate selection or mutational process.

Efficiency of replication of a replication-competent controlled herpesvirus relative to a replication-defective comparison virus or the wild type virus from which the replication-competent controlled virus was derived can be estimated by any method that allows for determinations of numbers of infectious virus (plaque-forming units or pfu) or numbers of viral particles. Biochemical methods for estimating viral replication efficiency can also be utilized. These methods will be aimed at quantifying amounts of viral DNA, RNA or protein products, and may include appropriate histochemical or immunohistochemical methods and biochemical assays of amplification and detection of nucleic acids (e.g., realtime PCR, RT-PCR, probe hybridization) or detection of viral protein products (e.g., western blot or other immunological assays). An activated replication-competent controlled virus would be said to replicate with greater efficiency than a comparison virus if higher levels of infectious virus or viral particles, or a biochemical correlate such as viral DNA, were measured at a time point after inoculation with equal numbers of infectious virus or viral particles at which (time point) the wild type virus from which the viruses being compared were derived would have completed essentially quantitatively one replication cycle. A not-activated replication-competent controlled virus would be said to replicate with lower efficiency than the wild type virus from which the replication-competent controlled virus was derived or a comparison virus if lower levels of infectious virus or viral particles, or a biochemical correlate such as viral DNA, were measured at a time point after inoculation with equal numbers of infectious virus or viral particles at which wild type virus would have completed essentially quantitatively at least one replication cycle. A measurement made at later time point would be accorded more weight than one made at an earlier time (only in the case of a comparison involving a not-activated replication-competent controlled virus). Typical in vitro experiments for the determination of replication efficiencies of activated replication-competent controlled viruses are single step growth curves. This type of experiment is also illustrated in the example section.

The term "essentially non-replicating" used to characterize the in vivo replication behavior of a not-activated replication-competent controlled virus means that the not-activated replication-competent controlled virus replicates with an efficiency that is at least 10 times lower than that of the wild type virus from which it was derived. More preferably, replication efficiency of the not-activated replication-competent controlled virus is at least 25 times lower than that of the wild type virus from which it was derived. Even more preferably, replication efficiency of the not-activated replication-competent controlled virus is at least 100 times lower than that of the wild type virus from which it was derived.

The term "replicates with a similarly low efficiency as a replication-defective comparison virus" refers to a replication efficiency of a not-activated replication-competent controlled virus that is no more than 10 times that of the comparison virus, preferably no more than 5 times that of the comparison virus, more preferably no more than twice that of the comparison virus and, most preferably, not detectably higher than that of the comparison virus. A five times higher replication efficiency refers to a determination of a five times higher number of not-activated replication-competent controlled virus or a five times higher level of its biochemical correlate than that determined for the comparison virus in the body region to which virus had been administered, whereby the determination is made at a time after the time point at which the wild type virus from which the viruses being compared were derived would have completed (essentially quantitatively) at least one replication cycle.

A "similar subject" refers to a subject from the same species, same sex and about the same age. The term can be understood as having a statistical meaning, in which case a similar subject that receives comparison virus is a group of subjects of the same mammalian species, of the same sex or mixture of sexes and of approximately same age or age distribution as the group of subjects receiving replication-competent controlled virus.

"in a similar composition, in a similar amount and to a similar body region" refers to a composition, amount or body region that is the same as the composition, amount or body region it is compared to or is as closely similar as can be achieved with a reasonable effort.

In specific embodiments, the vaccine compositions comprise a replication-competent controlled recombinant herpesvirus whose genome comprises a gene for a small-molecule regulator-activated transactivator which gene is functionally linked to a nucleic acid sequence that acts as a heat shock promoter or to a nucleic acid sequence that acts as a heat shock promoter as well as a transactivator-responsive promoter, and one or more transactivator-responsive promoters that are functionally linked to one or more viral genes required for efficient replication, also referred to as a replication-essential genes. Subsequent to administration of the virus to a body region of a mammalian subject, it can be activated by subjecting the body region to an activating heat dose in the presence of an effective concentration in the body region of an appropriate small-molecule regulator. Such an activation treatment results in one round of virus replication. For convenience, the latter replication-competent controlled herpesviruses are referred to herein as heat- and small-molecule regulator-activated viruses. The replication-competent controlled herpesvirus can further comprise an expressible heterologous gene (in addition to a gene encoding a (heterologous) transactivator) from another pathogen, an expressible heterologous gene encoding an immune-modulatory polypeptide or an expressible heterologous gene encoding another polypeptide, or any combination of such genes. Such heterologous genes can be expressed under the control of a transactivator-responsive promoter or of another promoter, e.g., a constitutively active promoter. For example, a heterologous gene for an immune-modulatory polypeptide can be a gene encoding a cytokine or a chemokine. A heterologous gene can also be a gene encoding a protein that facilitates local dissemination, infection or replication of the virus such as, e.g., a gene for a matrix metalloproteinase. A particular heterologous gene can be a gene for a protein (antigen) of another pathogen (i.e., a pathogen other than the replication-competent controlled virus or the wild type virus from which it was derived). For example, a replication-competent controlled herpesvirus of the invention can contain inserted in its genome an expressible gene for influenza surface antigen HA and/or NA. As a further example, a heterologous gene may encode a modified genomic RNA of a retrovirus that lacks terminal repeat sequences and when expressed gives rise to viral particles that are replication-defective. It is conceivable that such viral particles will be more potent immunogens than individually expressed viral proteins.

In other specific embodiments, the vaccine compositions comprise a replication-competent controlled recombinant herpesvirus whose genome comprises a gene for a small-molecule regulator-activated transactivator which gene is functionally linked to a nucleic acid sequence that acts as a constitutively active or a transactivator-enhanced promoter, a nucleic acid sequence that acts as a heat shock promoter that is functionally linked to a first replication-essential viral gene, and a transactivator-responsive promoter that is functionally linked to a second replication-essential viral gene. Subsequent to administration of the virus to a body region of a mammalian subject, it can be activated by subjecting the body region to an activating heat dose in the presence of an effective concentration in the body region of an appropriate small-molecule regulator. Such an activation treatment results in one round of virus replication. The replication-competent controlled recombinant virus can further comprise a heterologous gene from another pathogen, a heterologous gene encoding an immune-modulatory polypeptide or a heterologous gene encoding another polypeptide, or both. Such heterologous genes can be expressed under the control of a transactivator-responsive promoter or of another promoter, e.g., a constitutively active promoter. The latter replication-competent controlled herpesviruses are also referred to herein as heat- and small-molecule regulator-activated viruses. The term "transactivator-enhanced promoter" refers to a promoter that of necessity has some residual activity in the absence of transactivator and whose activity increases as function of increasing levels of transactivator (also termed an auto-activated promoter). A "transactivator-responsive promoter" is a promoter that ideally is inactive in the absence of the transactivator that activates it.

In yet other embodiments, the vaccine compositions comprise a replication-competent controlled recombinant herpesvirus whose genome comprises a gene for a small-molecule regulator-activated transactivator which gene is functionally linked to a nucleic acid sequence that acts as a constitutively active or a transactivator-enhanced promoter and a transactivator-responsive promoter that is functionally linked to a replication-essential viral gene. Subsequent to administration of the virus to a body region of a mammalian subject, it can be activated by subjecting the body region to an effective concentration of an appropriate small-molecule regulator. Such an activation treatment results in at least one round of virus replication. The replication-competent controlled virus can further comprise a heterologous gene from another pathogen, a heterologous gene encoding an immune-modulatory polypeptide or a heterologous gene encoding another polypeptide, or both. Such heterologous genes can be expressed under the control of a transactivator-responsive promoter or of another promoter, e.g., a constitutively active promoter. For convenience, the latter replication-competent, controlled viruses are referred to herein as small-molecule regulator-activated viruses.

In one embodiment, provided is a replication-competent controlled herpesvirus whose the genome comprises a gene for a small-molecule regulator-activated transactivator which gene is functionally linked to a nucleic acid sequence that acts as a heat shock promoter or to a nucleic acid sequence that acts as a heat shock promoter as well as a transactivator-responsive promoter, and one or more transactivator-responsive promoters that are functionally linked to one or more replication-essential viral genes wherein one of the replication-essential viral genes is the ICP4 gene or the ICP8 gene or two of the replication-essential viral genes are the ICP4 and ICP8 genes if the replication-competent controlled herpesvirus is derived from HSV-1 or HSV-2, or functional analogs or orthologs of these genes if the replication-competent controlled herpesvirus is derived from another herpesvirus. Also provided is a vaccine composition comprising such herpesvirus.

In one embodiment, provided is a replication-competent controlled herpesvirus whose the genome comprises a gene for a small-molecule regulator-activated transactivator which gene is functionally linked to a nucleic acid sequence that acts as a constitutively active or a transactivator-enhanced promoter, a nucleic acid sequence that acts as a heat shock promoter that is functionally linked to a first replication-essential viral gene and a transactivator-responsive promoter that is functionally linked to a second replication-essential viral gene wherein the second replication-essential viral genes is the ICP4 gene if the replication-competent controlled herpesvirus is derived from HSV-1 or HSV-2, or a functional analog or ortholog of this gene if the replication-competent controlled herpesvirus is derived from another herpesvirus. Also provided is a vaccine composition comprising such herpesvirus.

In one embodiment, provided is a composition comprising an effective amount of a replication-competent controlled herpesvirus for use in inducing protective immunity in a mammalian subject against the wild type virus from which the replication-competent controlled herpesvirus was derived, whereby the genome of the replication-competent controlled herpesvirus comprises a gene for a small-molecule regulator-activated transactivator which gene is functionally linked to a nucleic acid sequence that acts as a heat shock promoter or to a nucleic acid sequence that acts as a heat shock promoter as well as a transactivator-responsive promoter and one or more transactivator-responsive promoters that are functionally linked to one or more replication-essential viral genes, and protective immunity is induced by administering the composition to an area within or immediately beneath the skin or mucosal membrane of the mammalian subject, administering to the mammalian subject a composition comprising an effective amount of small-molecule regulator and subjecting said area to a heat treatment that results in activation of the replication-competent controlled herpesvirus.

A replication-competent controlled virus of the invention is derived from a virus of the herpesviridae family. In more specific embodiments, the replication-competent controlled recombinant herpesvirus is derived from a virus selected from an HSV-1, an HSV-2, a varicella zoster virus, a cytomegalovirus and a roseola virus.

Specific embodiments concern vaccine compositions comprising a heat- and small-molecule regulator-activated virus or a small-molecule regulator-activated virus, whereby the virus is derived from an HSV-1 or HSV-2 and a transactivator-controlled replication-essential viral gene is all copies of the ICP4 gene or the ICP8 gene. In a more specific embodiment, the virus is identical with HSV-GS1 or is derived from HSV-GS1. Further embodiments relate to compositions comprising a heat- and small-molecule regulator-activated virus or a small-molecule regulator-activated virus, whereby the virus is derived from an HSV-1 or HSV-2 and a first transactivator-controlled replication-essential viral gene is all copies of the ICP4 gene and a second transactivator-controlled or heat shock promoter-driven replication-essential viral gene is the ICP8 gene. In a more specific embodiment, the virus is identical with HSV-GS3 or is derived from HSV-GS3. In other embodiments, a heat- and small-molecule regulator-activated virus or small-molecule regulator-activated virus is derived from an HSV-1 or HSV-2 and lacks a functional ICP47 gene. This virus can be identical to or derived from HSV-GS4.

In particular embodiments of vaccine compositions comprising a heat- and small-molecule regulator-activated virus or a small-molecule regulator-activated virus, the small-molecule regulator-activated transactivator contains a ligand-binding domain from a progesterone receptor and is activated by a progesterone receptor antagonist or other molecule capable of interacting with the ligand-binding domain and of activating the transactivator. Alternatively, it contains a ligand-binding domain from an ecdysone receptor and is activated by an ecdysteroid, a diacylhydrazine or other molecule capable of interacting with the ligand-binding domain and of activating the transactivator. In yet another alternative, it contains a ligand-binding domain from a bacterial tetracycline repressor and is activated by a tetracycline or other molecule capable of interacting with the tetracycline repressor domain and of activating the transactivator. In yet another embodiment of compositions comprising a heat- and small-molecule regulator-activated virus or a small-molecule regulator-activated virus, the small-molecule regulator-activated transactivator contains a ligand-binding domain from an estrogen receptor and is activated by an estrogen receptor antagonist or other molecule capable of interacting with the ligand-binding domain and of activating the transactivator. In a further embodiment, the small-molecule regulator-activated transactivator is a complex of a polypeptide containing an FKBP12 sequence and a polypeptide containing an FRB sequence from mTOR, and is activated by rapamycin, a rapamycin derivative or other molecule capable of interacting with both polypeptides and of activating the transactivator.

A vaccine composition of the invention comprising a heat- and small-molecule regulator-activated herpesvirus or a small-molecule regulator-activated herpesvirus can further comprise a second virus that has a host range which overlaps that of the replication-competent controlled virus and has a replication-essential gene functionally linked to a transactivator-responsive promoter so that expression and activation of the transactivator of the replication-competent controlled virus also results in expression of the controlled replication-essential gene of the co-infecting second virus, thereby enabling replication of the second virus. The immune response elicited by the latter composition is expected to be directed not only against the replication-competent controlled virus but also against the second virus. The second virus can be an adenovirus, and the replication-essential gene (of the second virus) that is functionally linked to a transactivator-responsive promoter can be either the E1 or the E4 gene, or both of these genes.

Alternatively, a composition of the invention comprising a heat- and small-molecule regulator-activated herpesvirus or a small-molecule regulator-activated herpesvirus can further comprise a second virus that has a host range overlapping that of the replication-competent controlled virus, whereby the second virus lacks a replication-essential gene or only contains a nonfunctional version thereof and, consequently, can only replicate, if the missing functional product of the replication-essential gene is provided in trans. In this composition the replication-competent controlled virus comprises a functional version of the latter replication-essential gene (of the second virus) which gene is functionally linked to a transactivator-responsive promoter so that expression and activation of the transactivator of the replication-competent controlled virus also results in expression of the controlled replication-essential gene of the second virus, thereby complementing the second virus. The immune response elicited by the latter composition should not only be directed against the replication-competent controlled virus but also against the second virus. The second virus can be an adenovirus having a nonfunctional E1 and/or E4 gene and the replication-essential gene expressed from the replication-competent controlled virus can be the E1 and/or E4 gene.

Other embodiments concern vaccine compositions comprising an effective amount of a heat- and small-molecule regulator-activated herpesvirus or a small-molecule regulator-activated herpesvirus and an effective amount of a small-molecule regulator that is capable of activating the transactivator that controls replication of the heat- and small-molecule regulator-activated herpesvirus or the small-molecule regulator-activated herpesvirus.

The invention also relates to uses in immunization of a vaccine composition comprising an effective amount of a replication-competent controlled herpesvirus. In specific embodiments, the invention concerns the use in immunization of a composition comprising an effective amount of a heat- and small-molecule regulator-activated herpesvirus or of a small-molecule regulator-activated herpesvirus. The virus can comprise one or more of a heterologous gene from another pathogen, a heterologous gene encoding an immune-modulatory polypeptide or a heterologous gene encoding another polypeptide. Such heterologous genes can be expressed under the control of a transactivator-responsive promoter or of another promoter, e.g., a constitutively active promoter. Effective amounts of virus and small-molecule regulator can be present in the same composition. The latter composition is capable of inducing in a mammalian subject to which it is administered and thereafter subjected to activation treatment an immune response that is more effective in reducing infection by the wild type virus from which the replication-competent controlled virus was derived and/or in reducing disease severity, disease duration or mortality subsequent to infection with said wild type virus than the immune response induced in a similar subject by a replication-defective comparison virus (replication-competent controlled virus and comparison virus being administered in similar compositions, in similar amounts and to similar body regions of similar subjects).

The invention also encompasses methods of immunization in which compositions of the invention are administered to a subject. One embodiment of a method of immunization comprises (1) administering to a body region of a mammalian subject a composition of the invention comprising an effective amount of a heat- and small-molecule regulator-activated herpesvirus which may also contain an expressible heterologous gene, and (2) exposing said body region to an activating heat dose in the presence in the body region of an effective concentration of an appropriate small-molecule regulator (which is a small-molecule regulator capable of activating the transactivator of the heat- and small-molecule regulator-activated herpesvirus). In a related method, effective amounts of virus and small-molecule regulator are co-administered in a single composition, and the body region is exposed to an activating heat dose.

In a related method, a composition of the invention comprising an effective amount of a small-molecule regulator-activated herpesvirus which may also contain an expressible heterologous gene is administered to a body region, and the body region is exposed to an effective concentration of small-molecule regulator. In a further related method, effective amounts of virus and small-molecule regulator are co-administered in a single composition. In derivative methods of the above-described methods, a heat- and small-molecule regulator-activated herpesvirus can be activated a second or further time by a second or further exposure of the body region (inoculation region) to an activating heat dose in the presence of an effective concentration of small-molecule regulator, or a small-molecule regulator-activated virus can be re-activated by a second or further exposure of the body region to an effective concentration of small-molecule regulator (provided that the second or further activation occurs prior to viral clearance).

The body region (inoculation site region) to which a composition of the invention is administered can be any region on the surface of or within the body of a subject to which region an activating treatment, e.g., a heat dose and/or an effective dose of an appropriate small-molecule regulator, can be administered. The body region can be a cutaneous or subcutaneous region located anywhere on the trunk or the extremities of the subject. Preferably, administration of a composition can be to a cutaneous or subcutaneous region located on an upper extremity of the subject. Administration can also be to the lungs or airways, or a mucous membrane in an orifice of a subject. Another preferred body region is the nasal mucous membrane of a subject.

In one embodiment, provided is a method of immunization comprising: (1) administering to a body region of a mammalian subject a composition comprising an effective amount of a heat- and small-molecule regulator-activated virus, and (2) exposing said body region to an activating heat dose in the presence in the body region of an effective concentration of an appropriate small-molecule regulator (which is a small-molecule regulator capable of activating the transactivator of the heat- and small-molecule regulator-activated virus). In one embodiment, effective amounts of virus and small-molecule regulator are co-administered in a single composition, and the body region is exposed to an activating heat dose. In one embodiment, effective amounts of virus and small-molecule regulator are co-administered separately, and the body region is exposed to an activating heat dose. In one embodiment, the composition is any vaccine composition described herein. In one embodiment, the virus is any virus composition comprising a replication-competent controlled herpesvirus described herein. In one embodiment, the method is a method of immunizing a subject against a herpetic disease or condition. In one embodiment, steps (1) and (2) are repeated for one, two or more further cycles, optionally separated by at least a week, a month, etc. Optionally, administration of the composition can be to a cutaneous or subcutaneous region located on an extremity of the subject.

In one embodiment, provided is a method of achieving substantially one round of replication of a virus in a subject, comprising: (1) administering to a body region of a mammalian subject a composition comprising an effective amount of a heat- and small-molecule regulator-activated herpesvirus, and (2) exposing said body region to an activating heat dose in the presence in the body region of an effective concentration of an appropriate small-molecule regulator (which is a small-molecule regulator capable of activating the transactivator of the heat- and small-molecule regulator-activated herpesvirus). Optionally, multiple rounds of replication can be achieved by repeating step 2 within one to several days after the preceding activating treatment. In one embodiment, effective amounts of virus and small-molecule regulator are co-administered in a single composition, and the body region is exposed to an activating heat dose. In one embodiment, effective amounts of virus and small-molecule regulator are co-administered separately, and the body region is exposed to an activating heat dose. In one embodiment, the composition is any vaccine composition described herein. In one embodiment, the virus is any virus composition comprising a replication-competent controlled herpesvirus described herein. In one embodiment, the method is a method of immunizing a subject against a herpetic disease or condition. Optionally, administration of the composition can be to a cutaneous or subcutaneous region located on an extremity of the subject.

In one embodiment, provided is a method of manufacturing a replication-competent controlled herpesvirus, the method comprising
(i) preparing a first precursor recombination vector by inserting nucleic acid sequences from a selected wild type herpesvirus flanking the selected intragenic insertion site,
(ii) preparing a first recombination vector by inserting a transactivator gene cassette comprising a gene for a small-molecule regulator-activated transactivator which gene is functionally linked to a nucleic acid sequence that acts as a heat shock promoter or to a nucleic acid sequence that acts as a heat shock promoter as well as a transactivator-responsive promoter into the first precursor recombination vector in a site between the flanking viral nucleotide sequences,
(iii) introducing the gene cassette into the wild type herpesvirus genome by recombination in a cell co-transduced with the first recombination vector and wild type virion DNA, identifying a first recombinant virus by detecting the presence of the gene cassette in the genome of a progeny virus and preparing virion DNA therefrom,
(iv) preparing a second precursor recombination vector by inserting nucleic acid sequences from the wild type herpesvirus flanking the promoter region of a replication-essential viral gene selected for regulation,
(v) preparing a second recombination vector by inserting a transactivator-responsive promoter into the second precursor recombination vector in a site between the flanking viral nucleotide sequences,
(vi) introducing the transactivator-responsive promoter into the genome of the first recombinant virus by recombination in a cell co-transduced with the second recombination vector and virion DNA of the first recombinant virus, identifying second recombinant virus by detecting the presence of the transactivator-responsive promoter in the genome of a progeny virus and preparing a stock of the progeny virus containing both the transactivator gene cassette and a transactivator-regulated replication-essential viral gene. In one embodiment, the transactivator-responsive promoter is inserted into the wild type herpesvirus to produce a first recombinant virus and the transactivator cassette is inserted into the first recombinant virus.

Any of the methods can further be characterized as comprising any step described in the application, including notably in the "Detailed Description of the Invention"). The invention further relates to methods of identifying, testing and/or making compositions described herein. The disclosure further relates to pharmaceutical, notably vaccine, formulations of the compositions disclosed herein. The disclosure further relates to methods of using the compositions in methods of treatment or prevention of disease, e.g. a herpetic disease or condition.

DETAILED DESCRIPTION

Figure 1:
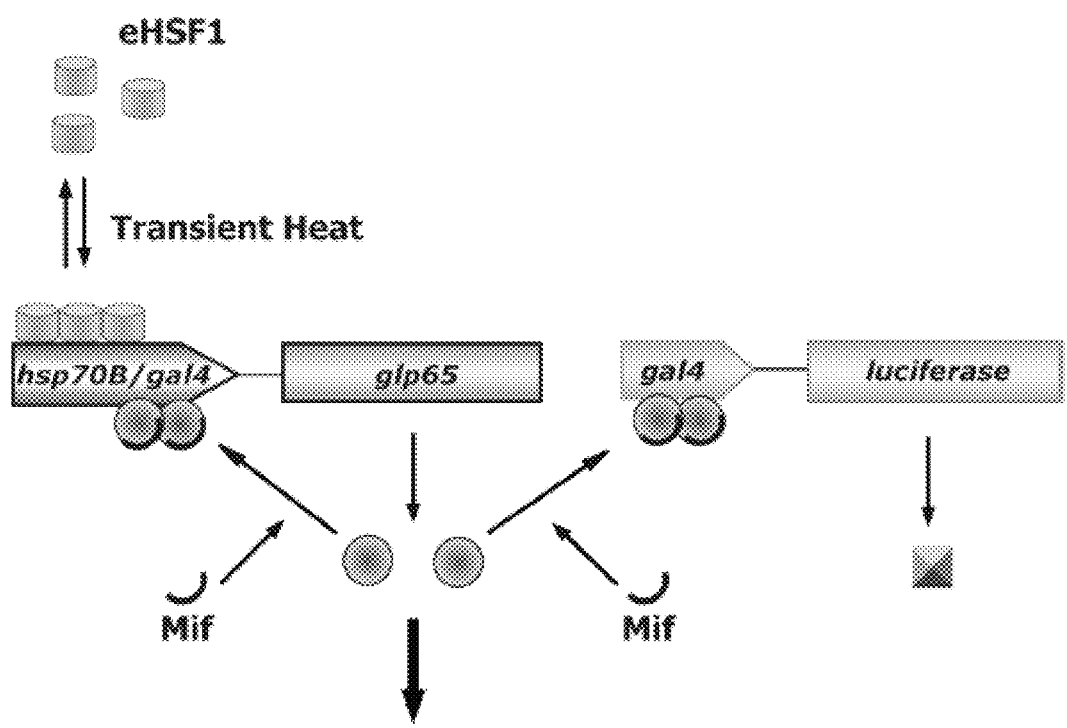
FIG. 1 presents an antiprogestin (mifepristone)-armed and heat-activated (or heat- and antiprogestin (mifepristone)-activated) SafeSwitch controlling a luciferase target gene. Reproduced from Vilaboa, N. and Voellmy, R. (2009) Deliberate regulation of therapeutic transgenes. In: Gene and Cell Therapy: Therapeutic Mechanisms and Strategies, Third Edition (Smyth Templeton, N. ed.) CRC Press, Boca Raton, Fla., pp. 619-36.
Figure 2:
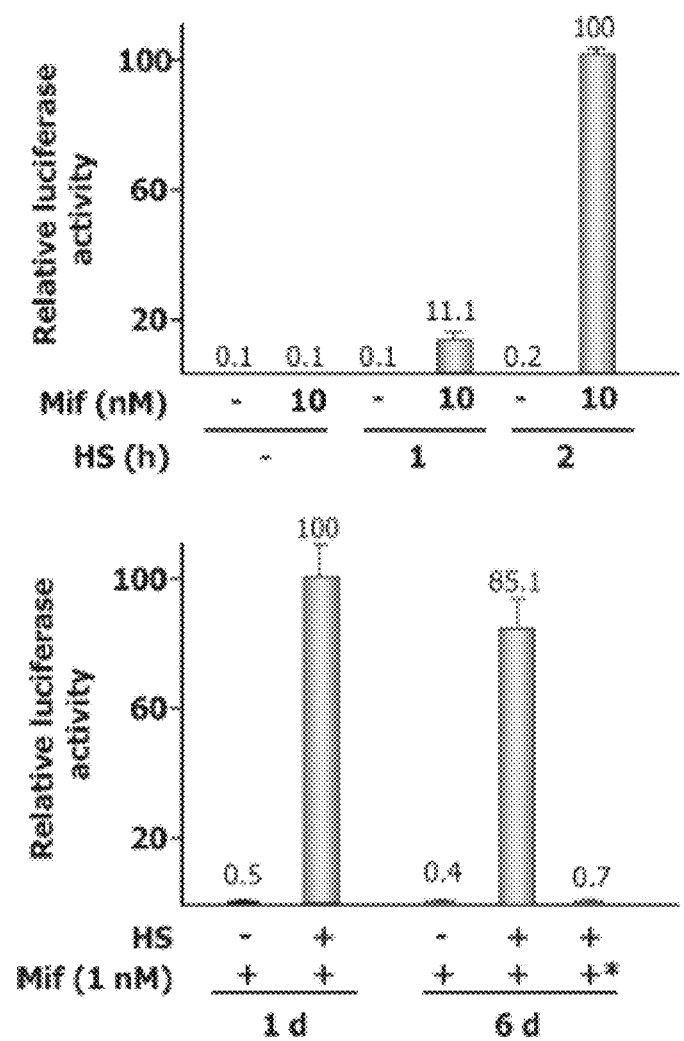
FIG. 2 relates to SafeSwitch performance in a stably transfected cell human line. Top panel: target gene activity one day after activating heat treatment (HS) at 43° C. Bottom panel: gene activity 1 day (1 d) and 6 days (6 d) after heat activation (43° C./2 h) in the presence of mifepristone (Mif), and reversibility of activation. *Mif was washed away one day after HS. Reproduced from Vilaboa, N. and Voellmy, R. (2009).

Unless otherwise defined below or elsewhere in the present specification, all terms shall have their ordinary meaning in the relevant art.

"Replication of virus" or "virus/viral replication" are understood to mean multiplication of viral particles. Replication is often measured by determination of numbers of infectious virus, e.g., plaque-forming units of virus (pfu). However, replication can also be assessed by biochemical methods such as methods that determine amounts of viral DNA, e.g., by a realtime PCR procedure, levels of viral gene expression, e.g., by RT-PCR of gene transcripts, etc. However, it is understood that marginal increases in levels of viral DNA or viral gene transcripts or protein products may not translate in corresponding marginal increases in virus replication due to threshold effects.

"Proteotoxic stress" is a physical or chemical insult that results in increased protein unfolding, reduces maturation of newly synthesized polypeptides or causes synthesis of proteins that are unable to fold properly.

A "small-molecule regulator" is understood to be a low molecular weight ligand of a transactivator used in connection with this invention. The small-molecule regulator is capable of activating the transactivator. The small-molecule regulator is typically, but not necessarily, smaller than about 1000 Dalton (1 kDa).

The term "transactivator" is used herein to refer to a non-viral and, typically, engineered transcription factor that when activated by a small-molecule regulator can positively affect transcription of a gene controlled by a transactivator-responsive promoter.

"Activated" when used in connection with a transactivated gene means that the rate of expression of the gene is measurably greater after activation than before activation. When used in connection with a transactivator, "active" or "activated" refers to a transactivation-competent form of the transactivator.

"Promoter of a heat shock gene", "heat shock gene promoter" and "heat shock promoter" are used synonymously. A "nucleic acid that acts as a heat shock promoter" can be a heat shock promoter or a nucleic acid that contains sequence elements of the type present in heat shock promoters which elements confer heat activation on a functionally linked gene.

Herein, a virus, whose genome includes a foreign (heterologous) non-viral or viral gene, is either referred to as a "virus" or a "viral vector".

A "replication-competent controlled virus" is a recombinant virus whose replicative ability is under the control of a gene switch that can be deliberately activated.

A "recombinant virus" refers specifically to a virus that has been altered by an experimenter. Often, a "recombinant virus" is simply referred to as a "virus".

A "replication-essential gene" or a "gene required for efficient replication" is arbitrarily defined herein as a viral gene whose loss of function diminishes replication efficiency by a factor of ten or greater. Replication efficiency can be estimated, e.g., in a single step growth experiment. For many viruses it is well known which genes are replication-essential genes. For herpesviruses see, e.g., Nishiyama, Y. (1996) Herpesvirus genes: molecular basis of viral replication and pathogenicitiy. Nagoya L. Med. Sci. 59: 107-19.

An "effective amount of a replication-competent controlled virus" is an amount of such virus that upon single or repeated administration to a subject followed by activation detectably enhances the subject's resistance to infection by the wild type virus from which the replication-competent controlled virus was derived and/or detectably reduces disease severity, disease duration or mortality subsequent to infection with said wild type virus. A corresponding amount of a replication-defective comparison virus, administered in a similar composition and to a similar body region of a similar subject induces a lower level of such functional immunity.

An "effective amount of a small-molecule regulator" is an amount that when administered to a subject by a desired route is capable of co-activating (in combination with a heat treatment) a heat- and small-molecule regulator-activated virus or activating a small-molecule regulator-activated virus with which the subject concurrently is, has been or will be inoculated to undergo a round of replication (or at least one round of replication in the case of a small-molecule regulator-activated virus) in the inoculation site region.

A "subject" or a "mammalian subject" is a mammalian animal or a human person.

A "heat shock gene" is defined herein as any gene, from any eukaryotic organism, whose activity is enhanced when the cell containing the gene is exposed to a temperature above its normal growth temperature. Typically, such genes are activated when the temperature to which the cell is normally exposed is raised by 3-10° C. Heat shock genes comprise genes for the "classical" heat shock proteins, i.e., Hsp110, Hsp90, Hsp70, Hsp60, Hsp40, and Hsp20-30. They also include other heat-inducible genes such as genes for MDR1, ubiquitin, FKBP52, heme oxidase and other proteins. The promoters of these genes, the "heat shock promoters", contain characteristic sequence elements referred to as heat shock elements (HSE) that consist of perfect or imperfect sequence modules of the type NGAAN or AGAAN, which modules are arranged in alternating orientations (Amin, J. et al. (1988) Key features of heat shock regulatory elements. Mol. Cell. Biol 8: 3761-3769; Xiao, H. and Lis, J. T. (1988) Germline transformation used to define key features of heat-shock response elements. Science 239: 1139-1142; Fernandes, M. et al. (1994) Fine structure analyses of the *Drosophila* and *Saccharomyces* heat shock factor—heat shock element interactions. Nucleic Acids Res. 22: 167-173). These elements are highly conserved in all eukaryotic cells such that, e.g., a heat shock promoter from a fruit fly is functional and heat-regulated in a frog cell (Voellmy, R. and Rungger, D. (1982) Transcription of a *Drosophila* heat shock gene is heat-induced in *Xenopus* oocytes. Proc. Natl. Acad. Sci. USA 79: 1776-1780). HSE sequences are binding sites for heat shock transcription factors (HSFs; reviewed in Wu, C. (1995) Heat shock transcription factors: structure and regulation. Annu. Rev. Cell Dev. Biol. 11, 441-469). The factor primarily responsible for activation of heat shock genes in vertebrate cells exposed to heat or a proteotoxic stress is heat shock transcription factor 1 (referred to herein as "HSF1") (Baler, R. et al. (1993) Activation of human heat shock genes is accompanied by oligomerization, modification, and rapid translocation of heat shock factor HSF1. Mol. Cell. Biol. 13: 2486-2496; McMillan, D. R. et al. (1998) Targeted disruption of heat shock factor 1 abolishes thermotolerance and protection against heat-inducible apoptosis. J. Biol. Chem. 273, 7523-7528). Preferred promoters for use in replication-competent controlled viruses discussed herein are those from inducible hsp70 genes. A particularly preferred heat shock promoter is the promoter of the human hsp70B gene (Voellmy, R. et al. (1985) Isolation and functional analysis of a human 70,000-dalton heat shock protein gene fragment. Proc. Natl. Acad. Sci. USA 82, 4949-4953).

"Vaccine" typically refers to compositions comprising microorganisms that are killed, replication-defective or otherwise attenuated. Herein, the term is expanded to also include compositions comprising replication-competent controlled viruses that can induce an immune response in the subject to which they are administered.

As was alluded to under Background, current thought appears to be that in order to be effective or more effective, respectfully, improved vaccine candidates for preventing or treating diseases such as herpes, HIV, tuberculosis or influenza need to elicit a balanced immune response that also includes a powerful effector T cell response. The present invention relates to replication-competent controlled viruses that, upon activation, replicate with efficiencies that approach those of the respective wild type viruses. The inventors hypothesized that these recombinant viruses and any heterologous protein they express will be potent immunogens that elicit balanced immune responses.

The proposed novel approach for immunization intends to bring to bear, in a carefully controlled fashion, the unattenuated replicative potential of the chosen viral vector. The underlying concept may be illustrated by reference to a historical approach for smallpox prevention known as variolation. Flower, D. R. (2008) Bioinformatics for vaccinology. John Wley & Sons; Henderson, D. A. et al. (2008) Smallpox and vaccinia. In: Vaccines (Plotkin, S. A. et al., eds.) 5th edition. 2008. Saunders Elsevier. The procedure that predates the first vaccine relates to the inoculation of a healthy person, typically subcutaneously, with dried scabs or pustular fluid from a person recovering from smallpox. When it was practiced routinely (until the beginning of the $19^{th}$ century in Europe and the United States, and until at least the second half of the $20^{th}$ century in remote parts of Africa and Asia), the procedure had a post-infection fatality rate of about 0.5-2%, which compared favorably with a mortality rate caused by the disease of about 20-30%. Variolation was effective in rendering a person immune against smallpox. While there may be several reasons why this procedure worked as well as it did, one appears to be related to the choice of inoculation site: smallpox (i.e., Variola virus) normally enters the lungs in the form of small aerosol droplets. From there the virus spreads rapidly. When inoculated subcutaneously, progress is less rapid, allowing the immune system to catch up with the disease at an early stage. Because of the substantial post-infection fatality rate, the variolation procedure was rapidly superseded by Edward Jenner's vaccination method when it became generally available. It is further noted that variolation suffered from another serious problem. Variolated persons were infectious for a certain period of time. During this period, especially since they typically were not or only mildly ill, they were capable of moving about and spreading the virus to naïve persons.

The general procedure exemplified by variolation of inducing immunity in a subject by administering a disease-causing microbial agent to an innocuous local site and allowing the agent to vigorously proliferate locally for a defined period of time so that strong innate and adaptive immune responses are triggered, could be made safe if (1) it could be assured that proliferation of the immunizing viral agent is restricted effectively to the chosen inoculation region as well as is narrowly limited in time, and (2) the possibility of recrudescence of significant virus replication at the inoculation site or elsewhere could be prevented and (3) the possibility of dissemination of disease-causing virus by immunized subjects could be excluded. The novel immunization method involving replication-competent controlled viruses discussed herein has been developed with the specific aim of providing this required safety. A wild type virus is genetically altered by placing at least one selected replication-essential gene under the control of a gene switch that has a broad dynamic range, i.e., that essentially functions as an on/off switch. Most preferred are heat- and small-molecule regulator-activated (dual-responsive) gene switches that were discussed, e.g., in Vilaboa, N. et al. (2011) Gene switches for deliberate regulation of transgene expression: recent advances in system development and uses. J. Genet. Syndr. Gene Ther. 2: 107. A particular gene switch of this kind, referred to as SafeSwitch (co-activated by heat and an antiprogestin), has been used in Examples and is illustrated in FIG. 1. Unless specifically indicated, the description that follows relates to viruses whose replication has been brought under the control of such a dual-responsive gene switch. However, the description is also relevant to other replication-competent controlled viruses of the invention (i.e., other heat- and small-molecule regulator-activated viruses and small-molecule regulator-activated viruses).

Replication of the so modified virus, a replication-competent controlled (recombinant) virus, only occurs when the dual-responsive gene switch is armed by an appropriate small-molecule regulator as well as is triggered by transient heat treatment (at a level below that causing burns or pain but above that which may be encountered in a feverish patient). Once the gene switch is activated, the virus expresses the full complement of viral proteins (or the desired complement of viral proteins and, optionally, heterologous RNA or proteins) and replicates with an efficiency approaching that of wild type virus.

Heat can be readily focused. Administering focused heat to a body region to which replication-competent controlled virus has been administered (i.e., the inoculation site) to trigger activation of the dual-responsive gene switch (in the presence of small-molecule regulator) will result in virus replication that is strictly confined to the heated region. The dual requirement for heat and a small-molecule regulator is intended to provide a high level of security against accidental virus replication. In the absence of small-molecule regulator, activation/re-activation of virus is virtually impossible. Similarly, in the absence of a concomitant heat treatment, virus replication is not normally activated.

The arming small-molecule regulator needs to satisfy a number of criteria. Most important will be that the substance is safe; adverse effects should occur at most at an extremely low rate and should be generally of a mild nature. Ideally, the chosen small-molecule regulator will belong to a chemical group that is not used in human therapy. However, before any substance not otherwise developed for human therapy could be used as small-molecule regulator in an immunization procedure, it would have to undergo extensive preclinical and clinical testing. It may be more efficacious to select a known and well-characterized drug substance that is not otherwise administered to the specific population targeted for immunization. Alternatively, a known drug substance may be selected that (1) will not need to be administered to subjects within at least the first several weeks after immunization and (2) is indicated only for short-term, sporadic administration, preferably under medical supervision. Thus, a potential low-level risk is further reduced by the avoidance of administration of the drug substance during the period during which immunizing virus is systemically present. Sporadic use of the drug substance under medical supervision will ensure that any significant inadvertent replication of immunizing virus would be rapidly diagnosed and antiviral measures could be taken without delay. In the example systems described herein, the arming small-molecule regulator is a progesterone receptor (PR) antagonist or antiprogestin, e.g., mifepristone or ulipristal. Mifepristone and ulipristal fulfill the latter requirements of not typically needing to be administered shortly after immunization, and of being used only infrequently (and only in a specific segment of the population) and only under medical supervision. Mifepristone and ulipristal have excellent safety records.

How the novel immunization method can be practiced is illustrated in the following specific example. A composition comprising an effective amount of a replication-competent controlled virus and an effective amount of a small-molecule regulator is administered to a subject intradermally or subcutaneously. Shortly after administration, a heating patch is activated and applied to the inoculation site by either the subject or the physician. Heating at about 43.5-45.5° C. (temperature of the patch surface in contact with the skin) will be for a period of about 10-60 min. The latter heat treatment will trigger one cycle of virus replication. If another round of replication is desired, another activated patch is applied to the inoculation site at an appropriate later time. If an immunization procedure involves sequential heat treatments, small-molecule regulator may also need to be administered sequentially. Alternatively, a slow release formulation may be utilized that assures the presence of an effective concentration of small-molecule regulator in the inoculation site region over the period during which viral replication is desired.

More generally, a body region to which a replication-competent controlled virus of the invention is administered, i.e., the inoculation site region, may be heated by any suitable method. Heat may be delivered or produced in the target region by different means including direct contact with a heated surface or a heated liquid, ultrasound, infrared radiation, or microwave or radiofrequency radiation. As proposed in the above specific example, a practical and inexpensive solution may be offered by heating patches (or similar devices of other shapes, e.g., cylinders or cones, for heating mucosal surfaces of the nose, etc.) containing a supercooled liquid that can be triggered by mechanical disturbance to crystallize, releasing heat at the melting temperature of the chemical used. A useful chemical may be sodium thiosulfate pentahydrate that has a melting temperature of about 48° C. U.S. Pat. Nos. 3,951,127, 4,379,448, and 4,460,546. The technology is readily available and is already being used in a number of health care products.

An "activating heat dose" is a heat dose that causes a transient activation of HSF1 in cells within the inoculation site region. Activation of this transcription factor is evidenced by a detectably increased level of RNA transcripts of a heat-inducible heat shock gene over the level present in cells not exposed to the heat dose. Alternatively, it may be evidenced as a detectably increased amount of the protein product of such a heat shock gene. Moreover, an activating heat dose may be evidenced by the occurrence of replication of replication-competent controlled virus in the presence of an effective concentration of an appropriate small-molecule regulator.

An activating heat dose can be delivered to the target region at a temperature between about 41° C. and about 47° C. for a period of between about 1 min and about 180 min. It is noted that heat dose is a function of both temperature and time of exposure. Hence, similar heat doses can be achieved by a combination of an exposure temperature at the lower end of the temperature range and an exposure time at the upper end of the time range, or an exposure temperature at the higher end of the temperature range and an exposure time at the lower end of the time range. Preferably, heat exposure will be at a temperature between about 42° C. and about 46° C. for a period of between about 5 min and about 150 min. Most preferably, heat treatment is administered at a temperature between about 43.5° C. and about 45.5° C. for a period of between about 10 min and about 60 min.

An effective concentration of a small-molecule regulator in the inoculation site region is a concentration that enables replication (one round) of replication-competent controlled virus in infected cells of that region that have also received an appropriate heat dose. What an effective concentration is depends on the affinity of the small-molecule regulator for its target transactivator. How such effective concentration is achieved and for how long it is maintained also depends on the pharmacokinetics of the particular small-molecule regulator, which in turn depends on the route of administration of the small-molecule regulator, the metabolism and route of elimination of the small-molecule regulator, the subject being examined, i.e., the type of subject (human or other mammal), its age, condition, weight, etc. It further depends on the type of composition administered, i.e., whether the composition permits an immediate release or a slow release of the regulator. For a number of well-characterized small-molecule regulator-transactivator systems, effective concentrations in certain experimental subjects have been estimated and are available from the literature. This applies to systems based on progesterone receptor, ecdysone receptors, estrogen receptors, and tetracycline repressor as well as to dimerizer systems, i.e., transactivators activated by rapamycin or analogs (including non-immunosuppressive analogs), or FK506 or analogs. For example, an effective concentration of mifepristone in rats can be reached by i.p. (intraperitoneal) administration of as little as 5 µg mifepristone per kg body weight (5 µg/kg). Amounts would have to be approximately doubled (to about 10 µg/kg), if the small-molecule regulator is administered orally. Wang, Y. et al. (1994) A regulatory system for use in gene transfer. Proc. Natl. Acad. Sci. USA 91: 8180-84. Such amounts of a small-molecule regulator that, upon administration by the chosen route, result in an effective concentration are referred to as effective amounts of the small-molecule regulator in question. How an effective amount of a small-molecule regulator that results in an effective concentration can be determined is well within the skills of an artisan and is also addressed in the example section.

In the afore-described specific example of how the novel immunization method may be practiced, a replication-competent controlled virus of the invention (a heat- and small-molecule regulator-activated virus) and an appropriate small-molecule regulator were co-administered in a single composition. Replication-competent controlled virus and small-molecule regulator can also be administered in separate compositions. Topical co-administration of immunizing virus and small-molecule regulator appears advantageous for several reasons, including minimization of potential secondary effects of the small-molecule regulator, further reduction of the already remote possibility that virus may replicate systemically during the immunization period, and minimization of the environmental impact of elimination of small-molecule regulator. Notwithstanding these advantages, the small-molecule regulator may be given by a systemic route, e.g., orally, which may be preferred if a formulation of the drug substance of choice is already available that has been tested for a particular route of administration. The relative timing of inoculation with replication-competent controlled virus, administration of an appropriate heat dose and administration of an effective amount of small-molecule regulator is derivative of the operational requirements of dual-responsive gene switch control. Typically, inoculation with immunizing virus will precede heat treatment. This is because heat activation of heat shock transcription factor (HSF1) is transient, and activated factor returns to an inactive state within at most a few hours after activation. The dual-responsive transactivator gene present in the viral genome must be available for HSF1-mediated transcription during the latter short interval of factor activity. For the latter gene(s) to become available for transcription, the immunizing virus will have had to adsorb to a host cell, enter the cell and unravel to present its genome to the cellular transcription machinery. Although not preferred, it is possible to heat-expose the inoculation site region immediately after (or even shortly before) administration of the immunizing virus. Typically, the inoculation site region is heat-exposed at a time between about 30 min to about 10 h after virus administration, although heat treatment may be administered even later. Regarding administration of the small-molecule regulator, there typically will be more flexibility because it will be possible to maintain an effective concentration systemically or specifically in the inoculation site region for one to several days. Consequently, small-molecule regulator can be administered prior to, at the time of or subsequent to virus administration, the only requirement being that the regulator be present in an effective concentration in the inoculation site region for the time needed for the target transactivator to fulfill its role in enabling viral replication. Typically, this time will correspond to that required for the completion of a round of induced virus replication. Typically, a round of virus replication will be completed within about one day.

As has been alluded to before, in the novel immunization method a replication-competent controlled virus may be induced to replicate once or several times. Replication may be re-induced one to several days after the previous round of replication. Such repeated replication will serve to increase viral load in the subject. For any round of replication to occur, the target cells that are infected with replication-competent controlled virus need to receive an activating heat dose and the tissue of which the latter cells are part (the inoculation region) must contain an effective concentration of small-molecule regulator.

Immunization can be by any suitable route, provided that a fraction of administered replication-competent controlled virus infects cells within a narrowly defined region that can be subjected to focused/localized heat treatment, and replication of the virus in the latter cells triggers the desired immune response (without causing disease or undue discomfort). The body region (inoculation site region) to which immunizing virus is administered may be a cutaneous or subcutaneous region located anywhere on the trunk or the extremities of the subject. Preferably, administration of a composition of the invention comprising a replication-competent controlled virus may be to a cutaneous or subcutaneous region located on an upper extremity of the subject. Administration may also be to the lungs or airways, or a mucous membrane in an orifice of a subject. This includes the nasal mucous membrane of a subject.

Dual-responsive gene switches consist of (1) a gene for a small-molecule regulator-activated transactivator, the gene being functionally linked to a promoter or promoter cassette responsive to heat and the transactivator and (2) a promoter responsive to the transactivator for controlling a gene of interest. Vilaboa, N. et al. (2005) Novel gene switches for targeted and timed expression of proteins of interest. Mol. Ther. 12: 290-8. FIG. 1 shows an example dual-responsive gene switch (the specific gene switch being referred to as "SafeSwitch") incorporating mifepristone (and ulipristal)-dependent chimeric transactivator GLp65 (or glp65). This transactivator comprises a DNA-binding domain from yeast transcription factor GAL4, a truncated ligand-binding domain from a human progesterone receptor and a transactivation domain from the human RelA protein. Burcin, M. M. et al. (1999) Adenovirus-mediated regulable target gene expression in vivo. Proc. Natl. Acad. Sci. USA 96: 355-60; Ye, X. et al. (2002) Ligand-inducible transgene regulation for gene therapy. Meth. Enzymol. 346: 551-61. In a cell containing gene switch and target gene, the target gene is not expected to be expressed in the absence of small-molecule regulator, e.g., mifepristone, or an activating heat treatment. When the cell is subjected to a heat treatment of an appropriate intensity, (endogenous) heat shock transcription factor 1 (HSF1) is activated, and transcription from the transactivator gene is initiated. A short time later, HSF1 is deactivated, and HSF1-driven expression of transactivator ceases. In the absence of small-molecule regulator, transactivator synthesized remains inactive and is eventually removed by degradation. However, in the presence of small-molecule regulator, transactivator is activated and mediates expression from its own gene as well as from the target gene. As a consequence, a certain transactivator level is maintained and target protein continues to be synthesized (theoretically) as long as small-molecule regulator remains present. Its withdrawal/removal causes inactivation of transactivator. Target as well as transactivator gene expression will diminish and eventually cease, and the system will reset itself.

The mifepristone-armed and heat-activated SafeSwitch was tested extensively in vitro in transient transfection and stable cell line formats and in vivo after electroporation of gene switch and target gene into mouse gastrocnemius muscle. Vilaboa et al. (2005). Results obtained from experiments with a cell line stably containing the gene switch and a luciferase target gene are reproduced in FIG. 2. The data reveal that the system performed as intended. Essentially no target protein expression occurred in the absence of mifepristone, even when cells were subjected to an activating heat treatment. Heat treatment in the presence but not in the absence of mifepristone resulted in activation of target gene expression. It is noted that the heat threshold was relatively elevated: even a 1-h heat treatment at 43° C. only resulted in submaximal activation. Activation of target gene expression was clearly heat dose-dependent. A single heat treatment induced sustained target gene expression for at least 6 days, but only in the continued presence of mifepristone. Removal of mifepristone subsequent to activation resulted in cessation of target gene expression (as evidenced by a disappearance of the labile target gene product).

Analogous dual-responsive gene switches that are activated by heat treatment in the presence of rapamycin or a non-immunosuppressive rapamycin derivative were also developed. Martin-Saavedra, F. M. et al. (2009) Heat-activated, rapamycin-dependent gene switches for tight control of transgene expression. Hum. Gene Ther. 20: 1060-1. Two different versions were prepared that are capable of trans-activating a target gene driven by a promoter containing ZFHD1-binding sites (as originally described in Rivera, V. M. et al. (1996) A humanized system for pharmacologic control of gene expression. Nat. Med. 2: 1028-32) or a GAL4 promoter, respectively.

Other examples for small-molecule regulator-activated transactivators than can be incorporated in dual-responsive gene switches or related gene switches include tetracycline/doxycycline-regulated tet-on repressors (Gossen, M. and Bujard, H. (1992) Tight control of gene expression in mammalian cells by tetracycline-responsive promoters. Proc. Natl. Acad. Sci. USA 89, 5547-5551; Gossen, M. et al. (1996) Transcriptional activation by tetracyclines in mammalian cells. Science 268, 1766-1769) and transactivators containing a ligand-binding domain of an insect ecdysone receptor (No, D. et al. (1996) Ecdysone-inducible gene expression in mammalian cells and transgenic mice. Proc. Natl. Acad. Sci. USA 93, 3346-3351). A stringently ligand-dependent transactivator of the latter type is the RheoSwitch transactivator developed by Palli and colleagues. Palli, S. R. et al. (2003) Improved ecdysone receptor-based inducible gene regulation system. Eur. J. Biochem. 270: 1308-15; Kumar, M. B. et al. (2004) Highly flexible ligand binding pocket of ecdysone receptor. A single amino acid change leads to discrimination between two groups of nonsteroidal ecdysone agonists. J. Biol. Chem. 279: 27211-18. The RheoSwitch transactivator can be activated by ecdysteroids such as ponasterone A or muristerone A, or by synthetic diacylhydrazines such as RSL-1 (also known as RH-5849, first synthesized by Rohm and Haas Company). Dhadialla, T. S. et al. (1998) New insecticides with ecdysteroidal and juvenile hormone activity. Annu. Rev. Entomol. 43: 545-69. Other small molecule-regulated transactivators may be used, provided that they can be employed to control the activity of a target gene without also causing widespread deregulation of genes of the host cell and provided further that the associated small-molecule regulators have acceptably low toxicity for the host at their effective concentrations.

Gene switches related to the above-discussed dual-responsive gene switches consist of (1) a gene for a small-molecule regulator-activated transactivator, the gene being functionally linked to a heat-responsive promoter, and (2) a promoter responsive to the transactivator for controlling a gene of interest. Unlike in the above-discussed dual-responsive gene switches, the transactivator gene is not auto-activated. As a consequence, the period of activity of such a gene switch subsequent to a single activating heat treatment is substantially shorter than that of a corresponding dual-responsive gene switch containing an auto-activated transactivator gene.

The novel immunization approach is exemplified herein by HSV-1-derived viruses. Other viruses including other types of herpesviruses can be employed as backbone for a replication-competent controlled virus of the invention. These include the alpha herpesviruses HSV2 and varicella zoster virus (VZV), beta herpesviruses including cytomegalovirus (CMV) and the roseola viruses (HSV6 and HSV7), and gamma herpesviruses such as Epstein-Barr virus (EBV) and Karposi's sarcoma-associated herpesvirus (KSHV). Preferred replication-competent controlled viruses of the invention are derived from HSV-1, HSV2 or varicella zoster viruses (VZV).

In a different embodiment, two replication-essential genes of a replication-competent controlled virus are not controlled by a dual-responsive gene switch that places them under dual control of heat and a small-molecule regulator, but are individually controlled by a heat shock promoter and a transactivator-responsive promoter (at least one replication-essential gene being controlled by a heat shock promoter and at least one replication-essential gene being controlled by a transactivator-responsive promoter). Transactivator is expressed from a constitutive promoter or from an auto-activated (transactivator-enhanced) promoter. If one replication-essential gene is controlled by a heat shock promoter and another by a promoter responsive to an activated transactivator, replication is also dually controlled by heat and a small-molecule regulator. However, a replication-competent controlled virus of this type is less preferred for several reasons. First, activated HSF1 and, consequently, heat shock promoters tend to be inactivated within a period of a few hours. Hence, if expressed under heat shock promoter control, certain viral genes may not be capable of fulfilling their normal role in the virus replication cycle. Second, also related to the transient nature of the heat shock response, if expression of two differently regulated viral genes (i.e., regulated by heat shock or transactivator, respectively) is required at different times in the virus life cycle, activating heat treatment and small-molecule regulator may need to be administered at different times, adding considerable inconvenience to an immunization procedure. A requirement that only genes that exhibit closely similar expression profiles be selected for regulation would represent a significant constraint on the design of a controlled virus. Finally, in the presence of one of the activating stimuli, i.e., heat or small-molecule regulator, one of the two differently regulated replication-essential genes will become activated, weakening the replication block. In the case where both replication-essential genes are dually regulated, neither of the genes will become active in the presence of ligand or if the host cell is exposed to heat. Hence, the stringent inhibition of replication will be maintained even in the presence of one of the activating stimuli. Regarding an appropriate heat dose for activation, nature and properties of transactivators, and properties and effective concentrations of virus and small-molecule regulators, etc., the reader is referred back to earlier sections of this specification.

In yet another less preferred embodiment, one or more replication-essential genes of a replication-competent controlled virus are not dually controlled by heat and a small-molecule regulator, but are singly controlled by a small-molecule regulator. A gene for a small-molecule regulator-activated transactivator is expressed from a constitutive promoter or from an auto-activated promoter. To achieve a degree of localization of virus replication, small-molecule regulator is also administered to the inoculation site, either together with the immunizing virus or separately. A slow release formulation may be utilized that assures the presence of an effective concentration of small-molecule regulator in the inoculation site region for the period during which viral replication is desired. Regarding the nature and properties of transactivators, and properties and effective concentrations of virus and small-molecule regulators, etc., the reader is referred back to earlier sections of this specification.

The replication-competent controlled viruses of the invention can also be utilized as vectors to deliver antigens from another infectious agent. Viruses of the herpesviridae family can accommodate sizeable DNA insertions in their genome, which insertions are not expected to reduce significantly replication efficiency. Inserted genes encoding, e.g., influenza virus surface antigens or internal proteins, HIV envelope or internal antigens, etc., may be subjected to heat and/or small molecule regulator control. This would link antigen expression to virus replication and restrict it to the inoculation site region. Alternatively, inserted genes may be placed under the control of other promoters, e.g., constitutive promoters, allowing for expression in non-productively infected cells, which would result in longer periods of antigen expression as well as expression in virus-infected cells outside of the inoculation site region.

Viruses have long been used as vehicles for delivery of antigens of another pathogen. Smith, G. L. et al. (1983) Infectious vaccinia virus recombinants that express hepatitis B virus surface antigen. Nature 302: 490-5; Moss, B. et al. (1984) Live recombinant vaccinia virus protects chimpanzees against hepatitis B. Nature 311: 67-9. Attenuated viral vectors employed included replication-defective viruses as well as viruses that retained some replication ability. Draper, S. J. and Heeney, J. L. (2010). Viruses as vaccine vectors for infectious diseases and cancer. Nat. Rev. 8: 62-71. Viral vectors studied included herpesviruses. There is evidence suggesting that attenuated replication-competent viruses induce superior and more balanced immune responses against expressed antigens than replication-defective viruses. Peng, B. et al. (2005) Replicating rather than non-replicating adenovirus-human immunodeficiency virus recombinant vaccines are better at eliciting potent cellular immunity and priming high-titer antibodies. J. Virol. 79: 10200-9; Halford, W. P. et al. (2006) ICP0 antagonizes Stat I-dependent repression of herpes simplex virus: implications for the regulation of viral latency. Virol. J. 3: 44; Huang, X. et al. (2009) A novel replication-competent vaccinia vector MVTT is superior to MVA for inducing high levels of neutralizing antibody via mucosal vaccination. PLoS ONE 4: e4180. We hypothesize that the replication-competent controlled viruses of the invention which replicate with near wild type efficiency will be similarly powerful or even more powerful "adjuvants" than attenuated viruses.

There have been concerns ultimately relating to the effectiveness of virally vectored vaccines. One issue has been whether vaccine vectors compete with transgene products for induction of immune responses. Paradoxically, strong immune responses to vector antigens may enhance immune responses to vector-expressed antigen(s) from another pathogen. Truckenmiller, M. E., Norbury, C. C. (2004) Viral vectors for inducing CD8 T cell responses. Exp. Opin. Biol. Ther. 4: 861-8. CD8 T cells can provide help for other responding CD8+ cells if present in sufficient numbers. Wang, B. et al. (2001) Multiple paths for activation of naïve CD8+ T cells: CD4-independent help. J. Immunol. 167: 1283-9.

Another concern has been whether pre-existing immunity to a virus will preclude its use as a vaccine vector. This issue not only relates to viruses such as adenoviruses and herpes viruses that are endemic but also to viruses that not normally infect humans but are used repeatedly as vaccine vectors. There may have been more serious concerns regarding the effects of pre-existing immunity to adenovirus (type 5) than to any other vector. Draper, S. J., Heeney, J. L. (2010). A recent study demonstrated that pre-existing immunity does not interfere with the generation of memory CD8 T cells upon vaccination with a heterologous antigen-expressing modified Ad5 vector, providing a basis for an efficient recall response and protection against subsequent challenge. Steffensen, M. A. et al. (2012) Pre-existing vector immunity does not prevent replication-deficient adenovirus from inducing efficient CD8 T-cell memory and recall responses. PLoS ONE 7: e34884. Furthermore, the transgene product-specific response could be boosted by re-vaccination. The issue of pre-existing immunity to herpesviruses has also been examined in multiple studies. Brockman, M. A. and Knipe, D. M. (2002) Herpes simplex virus vectors elicit durable immune responses in the presence of preexisting host immunity. J. Virol. 76: 3678-87; Chahlavi, A. et al. (1999) Effect of prior exposure to herpes simplex virus 1 on viral vector-mediated tumor therapy in immunocompetent mice. Gene Ther. 6: 1751-58; Delman, K. A. et al. (2000) Effects of preexisting immunity on the response to herpes simplex-based oncolytic therapy. Hum. Gene Ther. 11: 2465-72; Hocknell, P. K. et al. (2002) Expression of human immunodeficiency virus type 1 gp120 from herpes simplex virus type 1-derived amplicons result in potent, specific, and durable cellular and humoral immune responses. J. Virol. 76: 5565-80; Lambright, E. S. et al. (2000) Effect of preexisting anti-herpes immunity on the efficacy of herpes simplex viral therapy in a murine intraperitoneal tumor model. Mol. Ther. 2: 387-93; Herrlinger, U. et al. (1998) Pre-existing herpes simplex virus 1 (HSV-1) immunity decreases but does not abolish, gene transfer to experimental brain tumors by a HSV-1 vector. Gene Ther. 5: 809-19; Lauterbach, H. et al. (2005) Reduced immune responses after vaccination with a recombinant herpes simplex virus type 1 vector in the presence of antiviral immunity. J. Gen. Virol. 86: 2401-10; Watanabe, D. et al. (2007) Properties of a herpes simplex virus multiple immediate-early gene-deleted recombinant as a vaccine vector. Virology 357: 186-98. A majority of these studies reported little effect or only relatively minor effects on immune responses to herpesvirus-delivered heterologous antigens or on anti-tumor efficacy of oncolytic herpesviruses. Brockman, M. A. and Knipe, D. M. (2002); Chahlavi, A. et al. (1999); Delman, K. A. et al. (2000); Hocknell, P. K. et al. (2002); Lambright, E. S. et al. (2000); Watanabe, D. et al. (2007). Two studies were identified that reported substantial reductions of immune responses. Herrlinger, U. et al. (1998); Lauterbach, H. et al. (2005). However, it appears that the results of these studies may not be generalized because compromised models were employed. One of the studies employed a tumor model that was only barely infectable with the mutant HSV strain used. Herrlinger, U. et al. (1998). The other study employed a chimeric mouse immune model in combination with a severely crippled HSV strain (ICP4−, ICP22−, ICP27−, vhs−) as the test vaccine. Lauterbach, H. et al. (2005). All studies agreed that vaccine uses of herpesviruses are possible even in the presence of pre-existing immunity. It may be added that pre-existing immunity, e.g., to herpesviruses, may not be a general issue for childhood vaccination.

A replication-competent controlled virus of the invention can also be employed to control replication/propagation of a co-infecting second immunizing virus (or other microorganism). In the latter co-regulated virus, at least one replication-essential gene can be placed under the control of a promoter that is responsive to the small-molecule-activated transactivator of the replication-competent controlled virus. To provide an example, a co-regulated adenovirus may be constructed by replacing the E1 and/or the E4 promoter with a transactivator-responsive promoter. Among viruses that could possibly be co-regulated in this fashion by a replication-competent controlled herpesvirus of the invention are papillomaviruses (that also infect skin keratinocytes), certain polyomaviruses (that infect skin fibroblasts and keratinocytes) and parvovirus B19 (fifth disease; infects skin fibroblasts). It is noted that a co-regulated virus may naturally have an overlapping tropism with the regulating virus. In certain cases it may also be possible to generate a "matching tropism" by peudotyping. The group of viruses that may be co-regulated by a replication-competent controlled virus of the invention may be expanded further and may even include RNA viruses if co-regulation by means of regulated complementation is also taken into consideration. A pair of viruses (having overlapping tropisms) may, e.g., consist of a co-regulated virus that is defective for a replication-essential gene and a replication-competent controlled virus that expresses the latter replication-essential gene under control of a transactivator-responsive promoter.

Viruses have evolved a multitude of mechanisms for evading immune detection and avoiding destruction. Tortorella, D. et al. (2000) Viral subversion of the immune system. Annu. Rev. Immunol. 18: 861-926. Elimination or weakening of some of these mechanisms could further enhance the immunogenicity of an immunizing virus or viral vector. For example, HSV-1 and HSV-2 express protein ICP47. This protein binds to the cytoplasmic surfaces of both TAP1 and TAP2, the components of the transporter associated with antigen processing TAP. Advani, S. J. and Roizman, B. (2005) The strategy of conquest. The interaction of herpes simplex virus with its host. In: Modulation of Host Gene Expression and Innate Immunity by Viruses (ed. P. Palese), pp. 141-61, Springer Verlag. ICP47 specifically interferes with MHC class I loading by binding to the antigen-binding site of TAP, competitively inhibiting antigenic peptide binding. Virus-infected human cells are expected to be impaired in the presentation of antigenic peptides in the MHC class I context and, consequently, to be resistant to killing by CD8+ CTL. Deletion or disablement of the gene that encodes ICP47 ought to significantly increase the immunogenicity of the immunizing virus.

The role of ICP47 has been difficult to study in rodent models, because the protein is a far weaker inhibitor of mouse TAP than of human TAP. Still, one study was able to demonstrate that an HSV-1 ICP47-mutant was less neurovirulent than the corresponding wild type strain and that this reduced neurovirulence was due to a protective CD8 T cell response. Goldsmith, K. et al. (1998) Infected cell protein (ICP)47 enhances herpes simplex virus neurovirulence by blocking the CD8+ T cell response. J. Exp. Med. 187: 341-8. Latently infected neurons may exhibit infrequent but detectable expression of viral proteins. Feldman, L. T. et al. (2002) Spontaneous molecular reactivation of herpes simplex virus type 1 latency in mice. Proc. Natl. Acad. Sci. USA 99: 978-83. These proteins may be presented by MHC class I to specific CD8 T cells whose role it may be to prevent virus reactivation. Khanna, K. M. et al. (2004) Immune control of herpes simplex virus during latency. Curr. Opin. Immunol. 16: 463-69. Co-localization of CD8 T cells with infected cells in trigeminal ganglia has been observed. Khanna, K. M. et al. (2003) Herpes simplex virus-specific memory CD8 T cells are selectively activated and retained in latently infected sensory ganglia. Immunity 18: 593-603. That CD8 T cells control virus reactivation from latency and that this control is dependent on MHC class I presentation was demonstrated in a mouse study using HSV-1 recombinants that expressed cytomegalovirus MHC class I inhibitors. Orr, M. T. et al. (2007) CD8 T cell control of HSV reactivation from latency is abrogated by viral inhibition of MHC class I. Cell Host Microbe 2: 172-80. Hence, deletion of ICP47 is expected not only to enhance the immunogenicity of a replication-competent controlled virus but also to greatly reduce the already low probability of its inadvertent reactivation from latency.

The immunogenicity of an immunizing virus (i.e., a replication-competent controlled virus of the invention) may also be enhanced by including in the viral genome an expressible gene for a cytokine or other component of the immune system. A vaccination study in mice in which replication-defective herpesvirus recombinants expressing various cytokines were compared demonstrated that virus-expressed IL-4 and IL-2 had adjuvant effects. Osiorio, Y., Ghiasi, H. (2003) Comparison of adjuvant efficacy of herpes simplex virus type 1 recombinant viruses expressing $T_H1$ and $T_H2$ cytokine genes. J. Virol. 77: 5774-83. Further afield, modulation of dendritic cell function by GM-CSF was shown to enhance protective immunity induced by BCG and to overcome non-responsiveness to a hepatitis B vaccine. Nambiar, J. K. et al. (2009) Modulation of pulmonary DC function by vaccine-encoded GM-CSF enhances protective immunity against *Mycobacterium tuberculosis* infection. Eur. J. Immunol. 40: 153-61; Chou, H. Y. et al. (2010) Hydrogel-delivered GM-CSF overcomes nonresponsiveness to hepatitis B vaccine through recruitment and activation of dendritic cells. J. Immunol. 185: 5468-75.

An effective amount of a replication-competent controlled virus of the invention is an amount that upon administration to a subject and induced replication therein results in a detectably enhanced functional immunity of the subject (that is superior to the immunity induced by a replication-defective comparison virus). This enhanced functional immunity may manifest itself as enhanced resistance to infection or re-infection with a circulating (wild type) virus or may relate to enhanced suppression/elimination of a current infection. Hence, it may also manifest itself by a reduced disease severity, disease duration or mortality subsequent to infection with said wild type virus. Alternatively, or in addition, in the case of an immunizing virus expressing a foreign antigen, immunity can relate to preventive or therapeutic immunity against pathogens expressing and/or displaying the latter foreign antigen. It is noted that a number of factors will influence what constitutes an effective amount of a replication-competent controlled virus, including to some extent the site and route of administration of the virus to a subject as well as the activation regimen utilized (i.e., the relative timing of heating and small-molecule regulator administration, the heat dose(s) delivered to the inoculation site region, the number of replicative cycles induced, etc.). Effective amounts of a replication-competent controlled virus will be determined in dose-finding experiments. Generally, an effective amount of a replication-competent controlled virus of the invention will be from about $10^2$ to about $10^8$ plaque-forming units (pfu) of virus. More preferably, an effective amount will be from about $10^3$ to about $10^7$ pfu of virus, and even more preferably from about $10^3$ to about $10^6$ pfu of virus. Conceivably, an effective amount of a replication-competent controlled virus of the invention may be outside of the above ranges.

A vaccine composition of the invention will comprise an effective amount of a replication-competent controlled virus and, if a small-molecule regulator is also administered as part of the composition, an effective amount of the small-molecule regulator. Although it may be administered in the form of a fine powder under certain circumstances (as disclosed, e.g., in U.S. Pat. Appl. Publ. No 20080035143), a composition of the invention typically is an aqueous solution comprising a virus of the invention and, as the case may be, a small-molecule regulator. It may be administered (parenterally) to a subject as an aqueous solution or, in the case of administration to a mucosal membrane, as an aerosol thereof. See, e.g., U.S. Pat. No. 5,952,220. The compositions of the present invention will typically include a buffer component. The compositions will have a pH that is compatible with the intended use, and is typically between about 6 and about 8. A variety of conventional buffers may be employed such as phosphate, citrate, histidine, Tris, Bis-Tris, bicarbonate and the like and mixtures thereof. The concentration of buffer generally ranges from about 0.01 to about 0.25% w/v (weight/volume).

The compositions of the invention comprising a replication-competent controlled virus can further include, for example, preservatives, virus stabilizers, tonicity agents and/or viscosity-increasing substances. As mentioned before, they may also include an appropriate small-molecule regulator, or a formulation comprising such small-molecule regulator.

Preservatives used in parenteral products include phenol, benzyl alcohol, methyl paraben/propylparaben and phenoxyethanol. Phenoxyethanol is the most widely used preservative found in vaccines. Preservatives are generally used in concentrations ranging from about 0.002 to about 1% w/v. Meyer, B. K. 2007. Antimicrobial preservative use in parenteral products: past and present. J. Pharm. Sci. 96: 3155-67. Preservatives may be present in compositions comprising a replication-competent controlled virus at concentrations at which they do not or only minimally interfere with the replicative efficiency of the virus.

Osmolarity can be adjusted with tonicity agents to a value that is compatible with the intended use of the compositions. For example, the osmolarity may be adjusted to approximately the osmotic pressure of normal physiological fluids, which is approximately equivalent to about 0.9% w/v of sodium chloride in water. Examples of suitable tonicity adjusting agents include, without limitation, chloride salts of sodium, potassium, calcium and magnesium, dextrose, glycerol, propylene glycol, mannitol, sorbitol and the like, and mixtures thereof. Preferably, the tonicity agent(s) will be employed in an amount to provide a final osmotic value of 150 to 450 mOsm/kg, more preferably between about 220 and about 350 mOsm/kg and most preferably between about 270 and about 310 mOsm/kg.

If indicated, the compositions of the invention can further include one or more viscosity-modifying agents such as cellulose polymers, including hydroxypropylmethyl cellulose, hydroxyethyl cellulose, ethylhydroxyethyl cellulose, hydroxypropyl cellulose, methyl cellulose, carboxymethyl cellulose, glycerol, carbomers, polyvinyl alcohol, polyvinyl pyrrolidone, alginates, carrageenans, guar, karaya, agarose, locust bean gum, and tragacanth and xanthan gums. Such viscosity modifying components are typically employed in an amount effective to provide the desired degree of thickening. Viscosity-modifying agents may be present in compositions comprising a replication-competent controlled virus at concentrations at which they do not or only minimally interfere with infectivity and replicative efficiency of the virus.

If the composition also contains a small-molecule regulator, an effective amount of such small-molecule regulator can be included in the composition in the form of a powder, solution, emulsion or particle. As also provided before, an effective amount of a small-molecule regulator to be co-delivered with an effective amount of a replication-competent controlled virus will be an amount that yields an effective concentration of small-molecule regulator in the inoculation site region, which effective concentration enables at least one round of replication of the replication-competent controlled virus in infected cells of that region. To maintain a small-molecule regulator at an effective concentration for a more extended period, i.e., if replication of the virus (a heat- and small-molecule regulator-activated virus) is reinitiated by a second or further heat treatment of the inoculation site region, the small-molecule regulator may be included in the form of a slow-release formulation (see also below).

Methods for amplifying viruses are well known in the laboratory art. Industrial scale-up has also been achieved. For herpesviruses, see Hunter, W. D. (1999) Attenuated, replication-competent herpes simplex virus type 1 mutant G207: safety evaluation of intracerebral injection in nonhuman primates. J. Virol. 73: 6319-26; Rampling, R. et al. (2000) Toxicity evaluation of replication-competent herpes simplex virus (ICP34.5 null mutant 1716) in patients with recurrent malignant glioma. Gene Ther. 7: 859-866; Mundle, S. T. et al. (2013) High-purity preparation of HSV-2 vaccine candidate ACAM529 is immunogenic and efficacious in vivo. PLoS ONE 8(2): e57224.

Various methods for purifying viruses have been disclosed. See, e.g., Mundle et al. (2013) and references cited therein; Wolf, M. W. and Reichl, U. (2011) Downstream processing of cell culture-derived virus particles. Expert Rev. Vaccines 10: 1451-75.

While a small-molecule regulator can be co-administered with a replication-competent controlled virus in a single composition, a composition comprising a replication-competent controlled virus and a composition comprising a small-molecule regulator can also be administered separately. The latter composition will comprise an effective amount of a small-molecule regulator formulated together with one or more pharmaceutically acceptable carriers or excipients.

A composition comprising a small-molecule regulator may be administered orally, parenterally, by inhalation spray, topically, rectally, nasally, buccally, vaginally or via an implanted reservoir, preferably by oral administration or administration by injection. The compositions may contain any conventional non-toxic, pharmaceutically acceptable carriers, adjuvants or vehicles. In some cases, the pH of the formulation may be adjusted with pharmaceutically acceptable acids, bases or buffers to enhance the stability of the formulated small-molecule regulator or its delivery form. The term parenteral as used herein includes subcutaneous, intracutaneous, intravenous, intramuscular, intraarticular, intraarterial, intrasynovial, intrasternal, intrathecal, intralesional and intracranial injection or infusion techniques.

Liquid dosage forms of a small-molecule regulator for oral administration include pharmaceutically acceptable emulsions, microemulsions, solutions, suspensions, syrups and elixirs. In addition, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include, e.g., wetting agents, emulsifying and suspending agents, sweetening, flavoring, and perfuming agents.

Injectable preparations, for example sterile injectable aqueous or oleaginous suspensions, may be formulated according to the known art using suitable dispersing or wetting agents and suspending agents. The sterile injectable preparation may also be a sterile injectable solution, suspension or emulsion in a nontoxic, parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables. The injectable formulations can be sterilized, for example, by filtration through a bacteria-retaining filter, or by incorporating sterilizing agents in the form of sterile solid compositions which can be dissolved or dispersed in sterile water or other sterile injectable medium prior to use.

In order to prolong the effect of a small-molecule regulator, it may be desirable to slow the absorption of the compound from, e.g., subcutaneous (or, possibly, intracutaneous) or intramuscular injection. This may be accomplished by the use of a liquid suspension of crystalline or amorphous material with poor water solubility. The rate of absorption of the small-molecule regulator then depends upon its rate of dissolution, which, in turn, may depend upon crystal size and crystalline form. Alternatively, delayed absorption of a parenterally administered small-molecule regulator is accomplished by dissolving or suspending the compound in an oil vehicle. Injectable depot forms are made by forming microcapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing the small-molecule regulator with suitable non-irritating excipients or carriers such as cocoa butter, polyethylene glycol or a suppository wax which are solid at ambient temperature but liquid at body temperature and therefore melt in the rectum or vaginal cavity and release the small-molecule regulator.

Solid dosage forms for oral administration include capsules, tablets, pills, powders, and granules. In such solid dosage forms, the small-molecule regulator is mixed with at least one inert, pharmaceutically acceptable excipient or carrier such as sodium citrate or dicalcium phosphate and/or: a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the small-molecule regulator only, or preferentially, in a certain part of the intestinal tract, optionally, in a delayed manner. Examples of embedding compositions that can be used include polymeric substances and waxes.

Dosage forms for topical or transdermal administration of a small-molecule regulator include ointments, pastes, creams, lotions, gels, powders, solutions, sprays, inhalants or patches. The small-molecule regulator is admixed under sterile conditions with a pharmaceutically acceptable carrier and any preservatives or buffers as may be required.

The ointments, pastes, creams and gels may contain, in addition to a small-molecule regulator, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the small-molecule regulator, excipients such as lactose, talc, silicic acid, aluminum hydroxide, calcium silicates and polyamide powder, or mixtures of these substances. Sprays can additionally contain customary propellants such as chlorofluorohydrocarbons and replacements thereof.

Transdermal patches have the added advantage of providing controlled delivery of a compound to the body. Such dosage forms can be made by dissolving or dispensing the compound in the proper medium. Absorption enhancers can also be used to increase the flux of the compound across the skin.

For pulmonary delivery, a composition comprising an effective amount of a small-molecule regulator of the invention is formulated and administered to the subject in solid or liquid particulate form by direct administration e.g., inhalation into the respiratory system. Solid or liquid particulate forms of the small-molecule regulator prepared for practicing the present invention include particles of respirable size: that is, particles of a size sufficiently small to pass through the mouth and larynx upon inhalation and into the bronchi and alveoli of the lungs. Delivery of aerosolized therapeutics, particularly aerosolized antibiotics, is known in the art (see, for example U.S. Pat. Nos. 5,767,068 and 5,508,269, and WO 98/43650). A discussion of pulmonary delivery of antibiotics is also found in U.S. Pat. No. 6,014,969.

What an effective amount of a small-molecule regulator is will depend on the activity of the particular small-molecule regulator employed, the route of administration, time of administration, the stability and rate of excretion of the particular small-molecule regulator as well as the nature of the specific composition administered. It may also depend on the age, body weight, general health, sex and diet of the subject, other drugs used in combination or contemporaneously with the specific small-molecule regulator employed and like factors well known in the medical arts.

Ultimately, what is an effective amount of a small-molecule regulator has to be determined in dose-finding experiments, in which viral replication is assessed experimentally in the inoculation site region. Once an effective amount has been determined in animal experiments, it may be possible to estimate a human effective amount. "Guidance for Industry. Estimating the maximum safe starting dose for initial clinical trials for therapeutics in adult healthy volunteers", U.S. FDA, Center for Drug Evaluation and Research, July 2005, Pharmacology and Toxicology. For example, as estimated from rat data, an effective human amount of orally administered mifepristone (for enabling a single cycle of virus replication) will be between about 1 and about 100 µg/kg body weight.

If only a single round of replication of a replication-competent controlled virus of the invention is desired, small-molecule regulator may be administered to a subject as a single dose. However, the same amount may also be administered to a subject in divided doses. As discussed before, if multiple rounds of virus replication are desired to be induced within a relatively short period, an effective amount of a small-molecule regulator may be administered (once) in a slow release formulation that is capable of sustaining an effective concentration of small-molecule regulator for the period in question. Alternatively, an effective amount of a small-molecule regulator (that is capable of sustaining a single round of virus replication) can be administered repeatedly, whereby each administration is coordinated with the heat activation of virus replication (in the case of a heat- and small-molecule regulator-activated virus).

Recitation of ranges of values herein are merely intended to serve as a shorthand method of referring individually to each separate value falling within the range, unless otherwise indicated herein, and each separate value is incorporated into the specification as if it were individually recited herein.

The description herein of any aspect or embodiment of the invention using terms such as reference to an element or elements is intended to provide support for a similar aspect or embodiment of the invention that "consists of," "consists essentially of" or "substantially comprises" that particular element or elements, unless otherwise stated or clearly contradicted by context (e. g., a composition described herein as comprising a particular element should be understood as also describing a composition consisting of that element, unless otherwise stated or clearly contradicted by context).

This invention includes all modifications and equivalents of the subject matter recited in the aspects or claims presented herein to the maximum extent permitted by applicable law.

The present invention, thus generally described, will be understood more readily by reference to the following examples, which are provided by way of illustration and are not intended to be limiting of the present invention.

EXAMPLES

Example 1: Construction of Replication-Competent Controlled Viruses

All vectors were constructed using wild type HSV-1 strain 17syn+ as the backbone. This strain is fully virulent, is well characterized, and the complete genomic sequence is available. The generation of the viral recombinants was performed by homologous recombination of engineered plasmids along with purified virion DNA into rabbit skin cells (RS) by the calcium phosphate precipitation method as previously described. Bloom, D. C. 1998. HSV Vectors for Gene Therapy. Methods Mol. Med. 10: 369-386. All plasmids used to engineer the insertions of the transactivators or the GAL4-responsive promoters for recombination into the HSV-1 genome were cloned from HSV-1 strain 17syn+. Plasmid IN994 was created as follows: an HSV-1 upstream recombination arm was generated by amplification of HSV-1 DNA (17+) (from base pairs 95,441 to 96,090) with DB112 (5'GAG CTC ATC ACC GCA GGC GAG TCT CTT3') and DB113 (5'GAG CTC GGT CTT CGG GAC TAA TGC CTT3'). The product was digested with SacI and inserted into the SacI restriction site of pBluescript to create pUP. An HSV-1 downstream recombination arm was generated using primers DB115-KpnI (5'GGG GTA CCG GTT TTG TTT TGT GTG AC3') and DB120-KpnI (5'GGG GTA CCG GTG TGT GAT GAT TTC GC3') to amplify HSV-1 (17+ strain) genomic DNA sequence between base pairs 96,092 and 96,538. The PCR product was digested with KpnI, and cloned into KpnI digested pUP to create pIN994, which recombines with HSV-1 at the intergenic UL43/44 region.

HSV-GS1 contains a transactivator (TA) gene cassette inserted into the intergenic region between UL43 and UL44. In addition, the ICP4 promoter has been replaced with a GAL4-responsive promoter (GAL4-binding site-containing minimal promoter) in both copies of the short repeats. A first recombination plasmid pIN:TA1 was constructed by inserting a DNA segment containing a glp65 gene under the control of a promoter cassette that combined a human hsp70B promoter and a GAL4-responsive promoter (described in Vilaboa et al. 2005) into the multiple cloning site of plasmid pIN994, between flanking sequences of the HSV-1 UL43 and UL44 genes. The TA cassette was isolated from plasmid Hsp70/GAL4-GLP65 (Vilaboa et al. 2005) and was cloned by 3-piece ligation to minimize the region that was amplified by PCR. For the left insert, Hsp70/GAL4-GLP65 was digested with BamHI and BstX1 and the resulting 2875 bp band was gel purified. This fragment contains the Hsp70/GAL4 promoter cassette as well as the GAL4 DNA-binding domain, the progesterone receptor ligand-binding domain and part of the p65 activation domain of transactivator GLP65. The right insert was generated by amplifying a portion of pHsp70/GAL4-GLP65 with the primers TA.2803-2823.fwd (5'TCG ACA ACT CCG AGT TTC AGC3') (SEQ ID NO: 1) and BGHpA.rev (5' CTC CTC GCG GCC GCA TCG ATC CAT AGA GCC CAC CGC ATC C3') (SEQ ID NO: 2). The 763 bp PCR product was digested with BstX1 and NotI, and the resultant 676 bp band was gel-purified. This band contained the 3'end of the p65 activation domain and the BGHpA. For the vector, pIN994 was digested with BamHI and NotI, and the resulting 4099 bp fragment was gel-purified and shrimp alkaline phosphatase (SAP)-treated. The two inserts were then simultaneously ligated into the vector, creating an intact TA cassette. Subsequent to transformation, colony #14 was expanded, and the plasmid was verified by restriction enzyme analysis and then by sequence analysis.

One μg of pIN:TA1 was co-transfected with 2 μg of purified HSV-1 (17+) virion DNA into RS cells by calcium phosphate precipitation. The resulting pool of viruses was screened for recombinants by picking plaques, amplifying these plaques on 96 well plates of RS cells, and dot-blot hybridization with a $^{32}$P-labeled DNA probe prepared by labeling a TA fragment by random-hexamer priming. A positive well was re-plaqued and re-probed 5 times and verified to contain the TA by PCR and sequence analysis. This intermediate recombinant was designated HSV-17GS43.

A second recombination plasmid, pBS-KS:GAL4-ICP4, was constructed that contained a GAL4-responsive promoter inserted in place of the native ICP4 promoter by cloning it in between the HSV-1 ICP4 recombination arms in the plasmid pBS-KS:ICP4Δpromoter. This placed the ICP4 transcript under the control of the exogenous GAL4 promoter. This particular promoter cassette includes six copies of the yeast GAL4 UAS (upstream activating sequence), the adenovirus E1b TATA sequence and the synthetic intron Ivs8. This cassette was excised from the plasmid pGene/v5-HisA (Invitrogen Corp.) with AatII and HindIII, and the resulting 473 bp fragment was gel-purified. For the vector, pBS-KS:ICP4Δpromoter was digested with AatII and HindIII and the resulting 3962 bp fragment gel-purified and SAP-treated. Ligation of these two fragments placed the GAL4 promoter in front of the ICP4 transcriptional start-site. Subsequent to transformation, colony #5 was expanded, test-digested and verified by sequencing.

One μg of pBS-KS:GAL4-ICP4 was co-transfected with 4 μg of purified HSV-17GS43 virion DNA into cells of the ICP4-complementing cell line E5 (DeLuca, N. A. and Schaffer, P. A. 1987. Activities of herpes simplex virus type 1 (HSV-1) ICP4 genes specifying nonsense peptides. Nucleic Acids Res. 15: 4491-4511) by calcium phosphate precipitation. The resulting pool of viruses was screened for recombinants by picking plaques, amplifying these plaques on 96 well plates of E5 cells, and dot-blot hybridization with a $^{32}$P-labeled DNA probe prepared by labeling the GAL4-responsive promoter fragment by random-hexamer priming. A positive well was re-plaqued and re-probed 7 times and verified to contain the GAL4-responsive promoter in both copies of the short repeat sequences by PCR and sequence analysis. This recombinant was designated HSV-GS1.

To obtain pBS-KS:ΔSacI, the SacI site was deleted from the polylinker of plasmid vector pBluescript-KS+, by digesting the plasmid with SacI. The resulting 2954 bp fragment was gel-purified, treated with T4 DNA polymerase to produce blunt ends, re-circularized and self-ligated. Recombination plasmid BS-KS:ICP4Δpromoter was constructed as follows: to generate a first insert, cosmid COS48 (a gift of L. Feldman) was subjected to PCR with the primers HSV1.131428-131404 (5' CTC CTC AAG CTT CTC GAG CAC ACG GAG CGC GGC TGC CGA CAC G3') (SEQ ID NO: 3) and HSV1.130859-130880 (5' CTC CTC GGT ACC CCA TGG AGG CCA GCA GAG CCA GC3') (SEQ ID NO: 4). The primers placed HindIII and XhoI sites on the 5' end of the region and NcoI and KpnI sites on the 3' end, respectively. The 600 bp primary PCR product was digested with HindIII and KpnI, and the resulting 587 bp fragment was gel-purified. Vector pBS-KS:Δ.SacI was digested with HindIII and KpnI, and the resulting 2914 bp fragment was gel-purified and SAP-treated. Ligation placed the first insert into the vector's polylinker, creating pBS-KS:ICP4-3'end. To generate a second insert, cosmid COS48 was subjected to PCR with the primers HSV1.132271-132250 (5' CTC CTC GCG GCC GCA CTA GTT CCG CGT GTC CCT TTC CGA TGC3') (SEQ ID NO: 5) and HSV1.131779-131800 (5' CTC CTC CTC GAG AAG CTT ATG CAT GAG CTC GAC GTC TCG GCG GTA ATG AGA TAC GAG C3') (SEQ ID NO: 6). These primers placed NotI and SpeI sites on the 5' end of the region and AatII, SacI, NsiI, HindIII and XhoI sites on the 3' end, respectively. The 549 bp primary PCR product was digested with NotI and XhoI, and the resulting 530 bp band was gel-purified. This fragment also contained the 45 bp OriS hairpin. Plasmid BS-KS:ICP4-3' end was digested with NotI and XhoI and the resulting 3446 bp band was gel-purified and SAP-treated. Ligation generated pBS-KS:ICP4Δpromoter. The inserts in pBS-KS:ICP4Δpromoter were verified by sequence analysis.

HSV-GS2 contains transactivator (TA) gene cassette inserted into the intergenic region between UL37 and UL38. In addition, the ICP4 promoter has been replaced with a GAL4-responsive promoter (GAL4-binding site-containing minimal promoter) in both copies of the short repeats. A recombination plasmid, pUL37/38:TA, was constructed by inserting a DNA segment containing a glp65 gene under the control of a promoter cassette that combined a human hsp70B promoter and a GAL4-responsive promoter into the BspE1/AflIII site of plasmid pBS-KS:UL37/38, between flanking sequences of the HSV-1 UL37 and UL38 genes. The TA cassette was isolated from plasmid Hsp70/GAL4-GLP65 (Vilaboa et al. 2005) and was cloned by 3-piece ligation to minimize the region that was amplified by PCR. For the left insert, pHsp70/GAL4-GLP65 was digested with BamHI (filled in) and BstX1 and the resulting 2875 bp band was gel-purified. This fragment contains the Hsp70/GAL4 promoter cassette as well as the GAL4 DNA binding domain, the progesterone receptor ligand-binding domain and part of the p65 activation domain of transactivator GLP65. The right insert was generated by amplifying a portion of pHsp70/GAL4-GLP65 with the primers TA.2803-2823.fwd and BGHpA.rev. The 763 bp PCR product was digested with BstX1 and NotI (filled in), and the resultant 676 bp band was gel-purified. This band contained the 3'end of the p65 activation domain and the BGHpA. For the vector, pBS-KS:UL37/38 was digested with BspE1 and AflIII, and the resulting 3,772 bp fragment was filled in with T4 DNA polymerase, gel-purified and SAP-treated. The two inserts were then simultaneously ligated into the vector, creating an intact TA cassette. Following transformation, colonies were screened by restriction digestion. Colony #29 was expanded, and the plasmid verified by restriction enzyme analysis and then by sequence analysis.

One μg of pUL37/38:TA was co-transfected with 2 μg of purified HSV-1 (17+) virion DNA into RS cells by calcium phosphate precipitation. The resulting pool of viruses was screened for recombinants by picking plaques, amplifying these plaques on 96 well plates of RS cells, and dot-blot hybridization with a $^{32}$P-labeled DNA probe prepared by labeling a TA fragment by random-hexamer priming. A positive well was re-plaqued and re-probed 6 times and verified to contain the TA by PCR and sequence analysis. This intermediate recombinant was designated HSV-17GS38.

One µg of pBS-KS:GAL4-ICP4 was co-transfected with 5 µg of purified HSV-17GS38 virion DNA into E5 cells by calcium phosphate precipitation. The resulting pool of viruses were screened for recombinants by picking plaques, amplifying these plaques on 96 well plates of E5 cells, and dot-blot hybridization with a $^{32}$P-labeled DNA probe prepared by labeling the GAL4-responsive promoter fragment by random-hexamer priming. A positive well was re-plaqued and re-probed 7 times and verified to contain the GAL4-responsive promoter in both copies of the short repeat sequences by PCR and sequence analysis. This recombinant was designated HSV-GS2.

HSV-GS3 contains a transactivator (TA) gene cassette inserted into the intergenic region between UL43 and UL44. In addition, the ICP4 promoter has been replaced with a GAL4-responsive promoter (GAL4-binding site-containing minimal promoter) in both copies of the short repeats. Furthermore, the ICP8 promoter was replaced with a GAL4-responsive promoter. The construction of this recombinant virus involved placing a second HSV-1 replication-essential gene (ICP8) under control of a GAL4-responsive promoter. HSV-GS1 was used as the "backbone" for the construction of this recombinant. ICP8 recombination plasmid pBS-KS:GAL4-ICP8 was constructed. This plasmid contained a GAL4-responsive promoter inserted in place of the native ICP8 promoter by cloning it in between the HSV-1 ICP8 recombination arms in the plasmid pBS-KS:ICP8Δpromoter. This placed the ICP8 transcript under the control of the exogenous GAL4-responsive promoter. This particular promoter cassette consisted of six copies of the yeast GAL4 UAS (upstream activating sequence), the adenovirus E1 b TATA sequence and the synthetic intron Ivs8. This cassette was excised from the plasmid pGene/v5-HisA (Invitrogen Corp.) with AatII and HindIII, and the resulting 473 bp fragment gel-purified. For the vector, pBS-KS:ICP8Δpromoter was digested with AatII and HindIII, and the resulting 4588 bp fragment gel-purified and SAP-treated. Ligation of the latter two DNA fragments placed the GAL4-responsive promoter cassette in front of the ICP8 transcriptional start-site. Subsequent to transformation, colony #10 was expanded, test-digested and verified by sequencing.

One µg of pBS-KS:GAL4-ICP8 was co-transfected with 10 µg of purified HSV-GS1 virion DNA into E5 cells by calcium phosphate precipitation. Subsequent to the addition of mifepristone to the medium, the transfected cells were exposed to 43.5° C. for 30 minutes and then incubated at 37° C. Subsequently on days 2 and 3, the cells were again incubated at 43.5° C. for 30 minutes and then returned to 37° C. Plaques were picked and amplified on 96 well plates of E5 cells in media supplemented with mifepristone. The plates were incubated at 43.5° C. for 30 minutes 1 hour after infection and then incubated at 37° C. Subsequently on days 2 and 3, the plates were also shifted to 43.5° C. for 30 minutes and then returned to 37° C. After the wells showed 90-100% CPE, the plates were dot-blotted and the dot-blot membrane hybridized with a $^{32}$P-labeled DNA probe prepared by labeling the HSV-1 ICP8 promoter fragment that was deleted. A faintly positive well was re-plaqued and re-probed 8 times and verified to have lost the ICP8 promoter and to contain the GAL4-responsive promoter in its place by PCR and sequence analysis. This recombinant was designated HSV-GS3.

Recombination plasmid pBS-KS:ICP8Δpromoter was constructed using essentially the same strategy as that described above for the creation of pBS-KS:ICP4Δpromoter: a first insert was PCR-amplified from HSV-1 17syn+ virion DNA using the primers HSV1.61841-61865 (5' CTC CTC AGA ACC CAG GAC CAG GGC CAC GTT GG3') (SEQ ID NO: 7) and HSV1.62053-62027 (5' CTC CTC ATG GAG ACA AAG CCC AAG ACG GCA ACC3') (SEQ ID NO: 8) and subcloned to yield intermediate vector pBS-KS:ICP8-3' end. A second insert was similarly obtained using primers HSV1.62173-62203 (5' CTC CTC GGA GAC CGG GGT TGG GGA ATG AAT CCC TCC3') (SEQ ID NO: 9) and HSV1.62395-62366 (5' CTC CTC GCG GGG CGT GGG AGG GGC TGG GGC GGA CC3') (SEQ ID NO: 10) and was subcloned into pBS-KS:ICP8-3' end to yield pBS-KS:ICP8Δpromoter.

HSV-GS4: contains a transactivator (TA) gene cassette inserted into the intergenic region between UL43 and UL44. In addition, the ICP4 promoter has been replaced with a GAL4-responsive promoter (GAL4-binding site-containing minimal promoter) in both copies of the short repeats, and the ICP8 promoter has been replaced with a GAL4-responsive promoter. Furthermore, the US12 gene has been mutated to render its protein product (ICP47) nonfunctional. ICP47 amino acid residue K31 was changed to G31, and R32 to G32. Neumann, L. et al. (1997) J. Mol. Biol. 272: 484-92; Galocha, B. et al. (1997) J. Exp. Med. 185: 1565-72. A 500 bp ICP47 coding sequence-containing fragment was PCR-amplified from virion DNA of strain 17syn+. The fragment was PCR-amplified as two pieces (a "left-hand" and a "right-hand" piece), using two primer pairs. The mutations were introduced through the 5' PCR primer for the right-hand fragment. The resulting amplified left-hand and mutated right-hand fragments were subcloned into vector pBS, and the sequence in subclones was confirmed by sequence analysis. A subclone containing the 500 bp fragment with the desired mutations in ICP47 codons 31 and 32 was termed pBS:mut-ICP47.

One µg of pBS:mut-ICP47 was co-transfected with 10 µg of purified HSV-GS3 virion DNA into E5 cells by calcium phosphate precipitation. Subsequent to the addition of mifepristone to the medium, the transfected cells were exposed to 43.5° C. for 30 minutes and then incubated at 37° C. Subsequently on days 2 and 3, the cells were again incubated at 43.5° C. for 30 minutes and then returned to 37° C. Plaques were picked and amplified on 96 well plates of E5 cells in media supplemented with mifepristone. The plates were incubated at 43.5° C. for 30 minutes 1 hour after infection and then incubated at 37° C. Subsequently on days 2 and 3, the plates were also shifted to 43.5° C. for 30 minutes and then returned to 37° C. After the wells showed 90-100% CPE, the plates were dot-blotted and the dot-blot membrane hybridized with a $^{32}$P-labeled oligonucleotide probe to the mutated ICP47 region. A positive well was re-plaqued and re-probed several times and verified by sequence analysis to contain the expected mutated ICP47 gene sequence. This recombinant was designated HSV-GS4.

HSV-GS5 contains an expressible (auto-activated) trans-activator (TA) gene inserted into the intergenic region between UL43 and UL44. In addition, the ICP4 promoter has been replaced with a GAL4-responsive promoter (GAL4-binding site-containing minimal promoter) in both copies of the short repeats. A recombination plasmid pIN:TA2 is constructed by inserting a DNA segment containing an auto-activated glp65 gene into the multiple cloning site of plasmid pIN994, between flanking sequences of the HSV-1 UL43 and UL44 genes. The expressible TA gene is isolated from pHsp70/GAL4-GLP65 (Vilaboa et al. 2005) and pSwitch (Invitrogen life technologies), respectfully, and is cloned by 3-piece ligation to minimize the region that is amplified by PCR. For the left insert, pSwitch is digested with Ssp1 and BstX1, and a resulting 2425 bp band is gel purified. This fragment contains the auto-activated promoter as well as the GAL 4 DNA-binding domain, the progesterone receptor ligand-binding domain and part of the p65 activation domain of transactivator GLP65. The right insert is generated by amplifying a portion of pHsp70/GAL4-GLP65 with the primers TA.2803-2823.fwd and BGH-pA.rev. The 763 bp PCR product is digested with BstX1 and NotI, and the resultant 676 bp band is gel-purified. This band contains the 3'end of the p65 activation domain and the BGHpA. For the vector, pIN994 is first digested with BamHI, ends are filled in with Klenow DNA polymerase, and the DNA is further digested with NotI. The resulting 4099 bp fragment is gel-purified. The two inserts are then simultaneously ligated into the vector, creating an intact expressible TA gene. Subsequent to transformation, several colonies are expanded and plasmid DNAs subjected to restriction and then sequence analysis to identify pIN:TA2.

One μg of pIN:TA2 is co-transfected with 2 μg of purified HSV-1 virion DNA into RS cells by calcium phosphate precipitation. The resulting pool of viruses is screened for recombinants by picking plaques, amplifying these plaques on 96 well plates of RS cells, and dot-blot hybridization with a $^{32}$P-labeled DNA probe prepared by labeling a TA fragment by random-hexamer priming. A positive well is re-plaqued and re-probed several times and verified to contain the TA by PCR and sequence analysis. This intermediate recombinant is designated HSV-17GS43A.

One μg of pBS-KS:GAL4-ICP4 is co-transfected with 4 μg of purified HSV-17GS43A virion DNA into cells of the ICP4-complementing cell line E5 by calcium phosphate precipitation. The resulting pool of viruses is screened for recombinants by picking plaques, amplifying these plaques on 96 well plates of E5 cells, and dot-blot hybridization with a $^{32}$P-labeled DNA probe prepared by labeling the GAL4-responsive promoter fragment by random-hexamer priming. A positive well is re-plaqued and re-probed several times and verified to contain the GAL4-responsive promoter in both copies of the short repeat sequences by PCR and sequence analysis. This recombinant is designated HSV-GS5.

HSV-GS6 contains an auto-activated transactivator (TA) gene inserted into the intergenic region between UL43 and UL44. In addition, the ICP4 promoter is replaced with a GAL4-responsive promoter (GAL4-binding site-containing minimal promoter) in both copies of the short repeats. Furthermore, the ICP8 promoter is replaced with a human hsp70B promoter. The construction of this recombinant virus involves placing a second HSV-1 replication-essential gene (ICP8) under control of an Hsp70B promoter. HSV-GS5 is used as the "backbone" for the construction of this recombinant. ICP8 recombination plasmid pBS-KS:Hsp70B-ICP8 is constructed that contains an hsp70B promoter inserted in place of the native ICP8 promoter by cloning it in between the HSV-1 ICP8 recombination arms in the plasmid pBS-KS:ICP8Δpromoter. To isolate a human hsp70B promoter fragment, construct p17 is digested with BamHI, ends are filled in by Klenow DNA polymerase, and the DNA is further digested with HindIII. A 450 bp promoter fragment is gel-purified (Voellmy, R. et al. (1985) Proc. Natl. Acad. Sci. USA 82: 4949-53). For the vector, pBS-KS:ICP8Δpromoter is digested with ZraI and HindIII. The resulting 4588 bp fragment is gel-purified. Ligation of the latter two DNA fragments places the hsp70B promoter in front of the ICP8 transcriptional start-site. Subsequent to transformation, several colonies are expanded and plasmid DNAs subjected to restriction and then sequence analysis to identify pBS-KS:Hsp70B-ICP8.

One μg of pBS-KS:Hsp70B-ICP8 is co-transfected with 10 μg of purified HSV-GS5 virion DNA into E5 cells by calcium phosphate precipitation. The transfected cells are exposed to 43.5° C. for 30 minutes and then incubated at 37° C. Subsequently on days 2 and 3, the cells are again incubated at 43.5° C. for 30 minutes and then returned to 37° C. Plaques are picked and amplified on 96 well plates of E5 cells. The plates are incubated at 43.5° C. for 30 minutes a few hours after infection and then incubated at 37° C. Subsequently on days 2 and 3, the plates are also shifted to 43.5° C. for 30 minutes and then returned to 37° C. After the wells show 90-100% CPE, the plates are dot-blotted and the dot-blot membrane hybridized with a $^{32}$P-labeled DNA probe prepared by labeling the hsp70B promoter fragment by random-hexamer priming. A positive well is re-plaqued and re-probed several times and verified to have lost the ICP8 promoter and to contain the hsp70B promoter in its place by PCR and sequence analysis. This recombinant is designated HSV-GS6.

Generally known molecular biology and biochemistry methods were used. Molecular biology methods are described, e.g., in "Current protocols in molecular biology", Ausubel, F. M. et al., eds., John Wiley and Sons, Inc. ISBN: 978-0-471-50338-5.

Example 2: Regulated Replication of the Replication-Competent Controlled Viruses (a) Growth and Replication Properties of HSV-GS1 Plaque Analysis on Permissive (E5) and Non-Permissive (RS) Cells Serial dilutions of the purified HSV-GS1 virus were plated onto confluent monolayers of either rabbit skin (RS) or ICP4-complementing Vero-based helper cell line (E5) cells in 60 mm dishes. The virus was allowed to adsorb for 1 hour at 37° C., and then the inoculum was removed, and the cells were overlayed with complete medium (Modified Eagles Medium supplemented with 5% calf serum or 10% fetal bovine serum for RS or E5 cells, respectively). The dishes were then incubated 72 hours and stained with crystal violet to visualize any viral plaques. At dilutions resulting in 10-100 plaques on E5 cells, no plaques were observed on the non-complementing RS cells.

Growth Analysis of HSV-GS1

Confluent monolayers of either RS or E5 cells in 60 mm dishes were infected as described above with HSV-GS1 at a multiplicity-of-infection (m.o.i.) of 5, incubated for 48 hours, harvested by scraping cells into the medium, frozen at −80° C., subjected to 2 rounds of freezing-thawing and titrated for infectious virus. Results are shown in Table 1.

TABLE 1

Titration of viruses in RS and E5 cells

| Virus | RS cells | E5 cells |
| --- | --- | --- |
| 17syn+ | $8.3 \times 10^8$ pfu/ml | $1.2 \times 10^7$ pfu/ml |
| HSV-GS1 | ND* | $4.0 \times 10^7$ pfu/ml |

*ND = None detected. (Detection limit in this experiment was about 100 PFU.)

Figure 3:
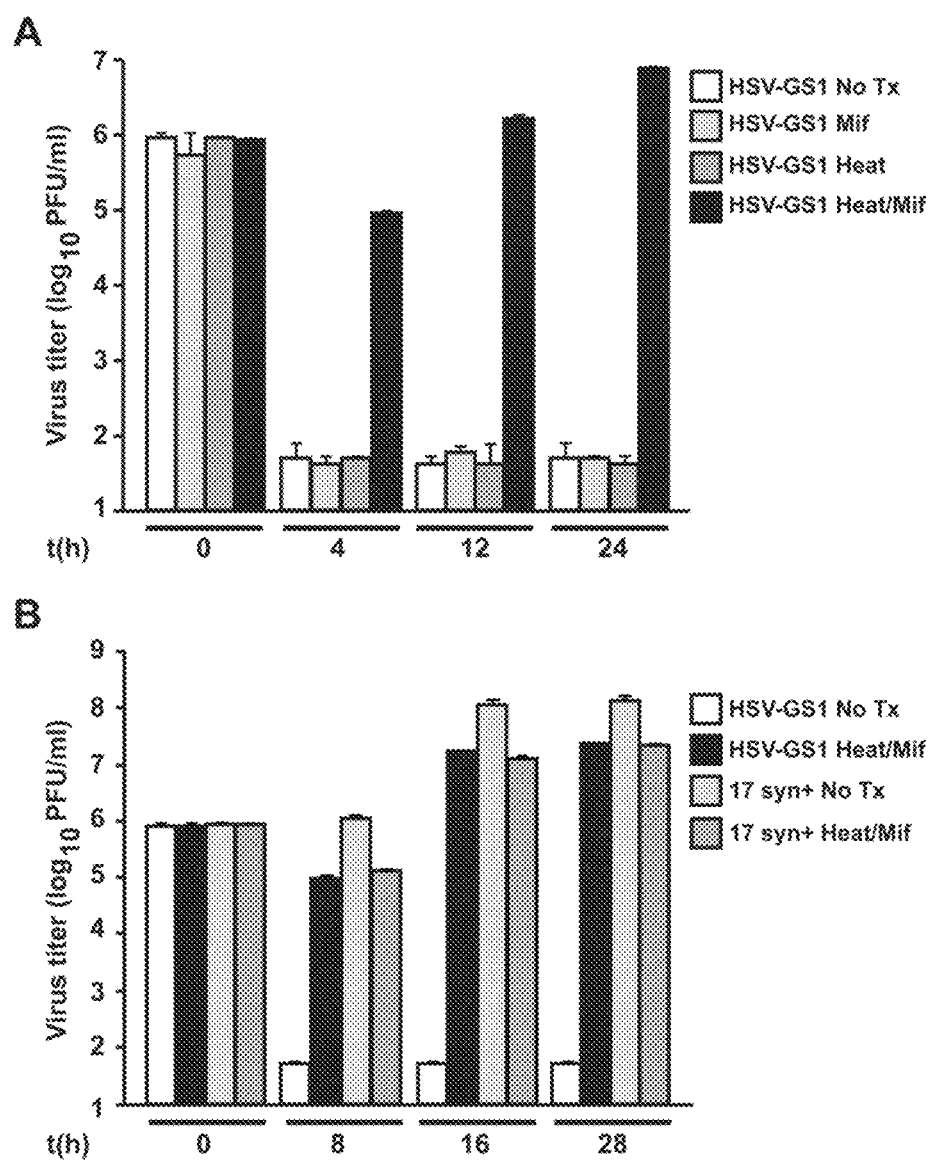
FIG. 3 relates to single step growth experiments with HSV-GS1 in Vero cells. (A) Controllability of replication. Four basic conditions were tested: (1) heat treatment at 43.5° C. for 30 min in the presence of 10 nM mifepristone (activating treatment), (2) heat treatment alone, (3) mifepristone exposure alone, and (4) no treatment. Heat treatment was administered immediately after infection (i.e., immediately after removal of the viral inoculum). (B) Comparison of replication efficiencies of wild type strain 17syn+ and HSV-GS1 with or without activating treatment. Heat treatment was applied 4 h after infection. Mif: mifepristone. PFU/ml values and standard deviations are shown.

Analysis of the Effects of Heat Exposure and Mifepristone on the Replication of HSV-GS1 in Vero Cells The purpose of this experiment was to compare the replication cycle of HSV-GS1 with the wild type vector HSV-1 strain 17syn+. Confluent monolayers of Vero cells were infected with either HSV-1 strain 17+ or the recombinant HSV-GS1 at an m.o.i. of 3. The virus was allowed to adsorb for 1 hour at 37° C., and then the inoculum was removed, and the cells were overlayed with complete medium (Modified Eagles Medium supplemented with 10% fetal bovine serum). Heat treatment was performed 4 hours after adsorption by floating the sealed dishes in a 43.5° C. water bath for 30 minutes. Mifepristone treatment (10 nM) was initiated at the time of the initial infection. The dishes were then incubated for 72 hours at 37° C. At 0, 8, 16 and 28 hours post-infection, two dishes were removed, the cells scraped into the media to harvest, and subjected to 2 freeze-thaw cycles. The infectious virus was then determined by titrating the lysate of each dish in triplicate on 24-well plates of confluent E5 cells. Plaques were visualized after 2 days by staining with crystal violet. Results demonstrate that under the chosen experimental conditions HSV-GS1 replicates as efficiently as wild type virus 17syn+(FIG. 3B). No replication of HSV-GS1 appears to occur in the absence of an activation treatment (heat and mifepristone). It is also noted that the activating treatment, i.e., heat exposure and incubation in the presence of mifepristone, only slightly affected wild type virus replication.

Analysis of the Dependence of HSV-GS1 Replication on Both Heat Exposure of the Host Cell and the Presence of Small-Molecule Regulator The purpose of this experiment was to determine whether the activation of the HSV-GS1 recombinant by heat and mifepristone was due to a requirement of both, and that mifepristone alone or heat alone was not sufficient to induce replication. The experiment was performed as described in the preceding section with the exception that heat treatment was administered immediately after adsorption. The data show that replication of HSV-GS1 did not occur unless the host cells were exposed to heat in the presence of mifepristone (FIG. 3A).

(b) Growth and Replication Properties of HSV-GS3

Replication Efficiency of HSV-GS3

Figure 4:
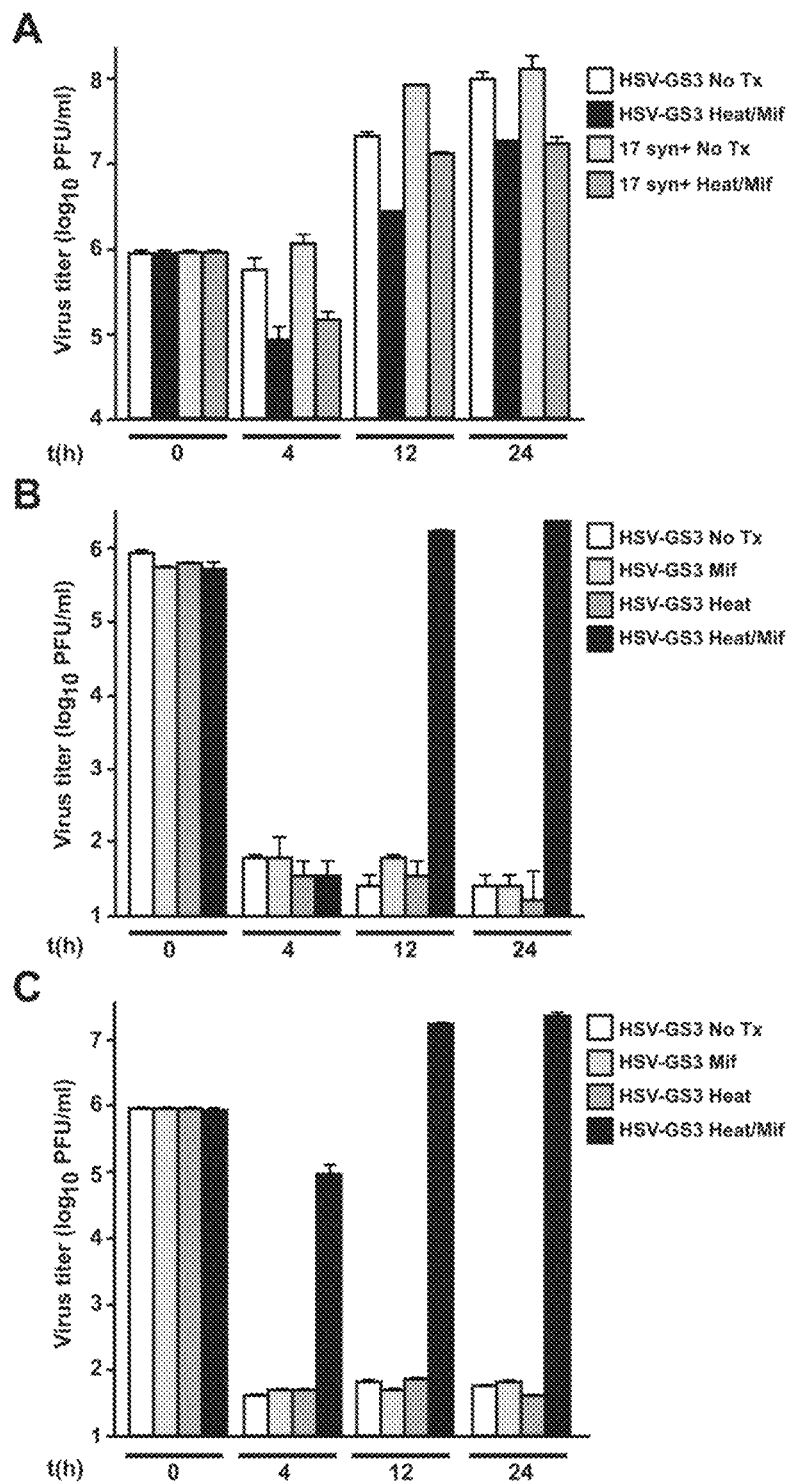
FIG. 4 relates to single step growth experiments with HSV-GS3. (A) Comparison of replication efficiencies of wild type strain 17syn+ and HSV-GS3 with or without activating treatment in E5 cells (17syn+) or E5 cells transfected with an ICP8 expression plasmid (HSV-GS3). (B) Regulation of replication of HSV-GS3 in Vero cells. See the legend to FIG. 3 for a description of the four basic conditions tested (C) Analogous experiment in SCC-15 cells. In these experiments, heat treatments were administered immediately after infection. PFU/ml values and standard deviations are shown.

The purpose of this experiment was to compare the replication cycle of the HSV-GS3 recombinant with the wild type vector HSV-1 17syn+. Confluent monolayers of E5 cells (but see below) were infected with either HSV-1 strain 17+ or the recombinant HSV-GS3 at an m.o.i. of 3. Virus was allowed to adsorb for 1 hour at 37° C. and then the inoculum was removed and the cells overlayed with complete medium (Modified Eagles Medium supplemented with 10% fetal bovine serum). Heat treatment was performed after adsorption by floating the sealed dishes in a 43.5 C water bath for 30 minutes at 4 hours post infection. Mifepristone treatment (10 nM) was initiated at the time of the initial infection. For the HSV-GS3 No Tx (no treatment) set, the E5 cells were transfected with a plasmid containing an expressible ICP8 gene 12 hours prior to infection. The dishes were then incubated further at 37° C. At 0, 4, 12 and 24 hours post-infection, two dishes were removed, the cells scraped into the media to harvest, and subjected to 2 freeze-thaw cycles. The infectious virus was then determined by titrating the lysate of each dish in triplicate on 24-well plates of confluent E5 cells previously transfected with ICP8 expression plasmid. Plaques were visualized after 2 days by staining with crystal violet. Results indicate that HSV-GS3 replicated nearly as efficiently as wild-type virus HSV-1 17syn+ under the chosen experimental conditions (FIG. 4A).

Analysis of the Dependence of HSV-GS3 Replication on Both Heat Exposure of the Host Cell and the Presence of Small-Molecule Regulator Single-step growth experiments were carried out to determine whether the activation of HSV-GS3 by heat and mifepristone was due to a requirement of both, and that mifepristone alone or heat alone was not sufficient to induce replication. The experiment shown in FIG. 4B was performed as described in the preceding section with the exception that Vero cells were used and heat treatment was administered immediately after adsorption. Titrations were in E5 cells previously transfected with ICP8 expression plasmid. A similar experiment was carried out with human squamous cell tumor line SCC-15 (FIG. 4C). The results of the latter experiments demonstrate that replication of HSV-GS3 is tightly regulated. It is only triggered by heat exposure of infected cells in the presence of mifepristone.

In other experiments, measurement of virus replication by titration of infectious virus was substituted by methods of quantification of viral DNA or expression of viral genes. In these experiments mifepristone and/or ulipristal (small-molecule regulators) were tested. One such experiment had the design summarized in Table 2.

TABLE 2

| Treatment groups | | | | | | |
|---|---|---|---|---|---|---|
| | Ulipristal | | | | Mifepristone | No drug |
| | 0.1 nM | 0.3 nM | 1 nM | 10 nM | 10 nM | — |
| Heat treatment | X | X | X | X | X | X |
| No heat treatment | | | | X | X | X |

Thirty-five mm dishes of confluent Vero cells were infected at an m.o.i. of 3 with the HSV-GS3 vector. Each treatment group consisted of 3 replicate dishes (for each time point). Virus was adsorbed for 1 hour at 37° C., the inoculum removed, and the cells overlayed with complete medium (Modified Eagles Medium supplemented with 10% fetal bovine serum). Drug (i.e., mifepristone or ulipristal) treatment was initiated at the time of the initial infection. Heat treatment was performed after adsorption by floating the sealed dishes in a 43.5° C. water bath for 30 minutes on a submerged platform (initiated 4 hours post infection). Dishes were incubated further at 37° C. At 1, 4, 12 and 24 h post heat treatment, three dishes were removed, the media removed, and the DNA and RNA extracted using TRIzol. Extracted DNA was subjected to Taqman Realtime PCR for quantitative analysis for HSV-1 DNA (using HSV DNA polymerase primers/probe). Extracted RNA was analyzed by Taqman RT-PCR for the presence of ICP4 and glycoprotein C (gC) transcripts. DNA and RNA quantities were normalized relative to the cellular gene APRT and presented as relative quantities. Primers used are shown in Table 3 below.

TABLE 3

```
Primers and probes used for qPCR

HSV DNA    F  AGAGGGACATCCAGGACTTTGT (SEQ ID NO: 11)
Pol
           R  CAGGCGCTTGTTGGTGTAC (SEQ ID NO: 12)
           P  ACCGCCGAACTGAGCA (SEQ ID NO: 13)

ICP4       F  CACGGGCCGCTTCAC (SEQ ID NO: 14)
           R  GCGATAGCGCGCGTAGA (SEQ ID NO: 15)
           P  CCGACGCGACCTCC (SEQ ID NO: 16)

gC         F  CCTCCACGCCCAAAAGC (SEQ ID NO: 17)
           R  GGTGGTGTTGTTCTTGGGTTTG (SEQ ID NO: 18)
           P  CCCCACGTCCACCCC (SEQ ID NO: 19)

Mouse      F  CTCAAGAAATCTAACCCCTGACTCA
APRT          (SEQ ID NO: 20)
           R  GCGGGACAGGCTGAGA (SEQ ID NO: 21)
           P  CCCCACACACACCTC (SEQ ID NO: 22)
```

F: forward; R: reverse; P: probe.

Figure 5:
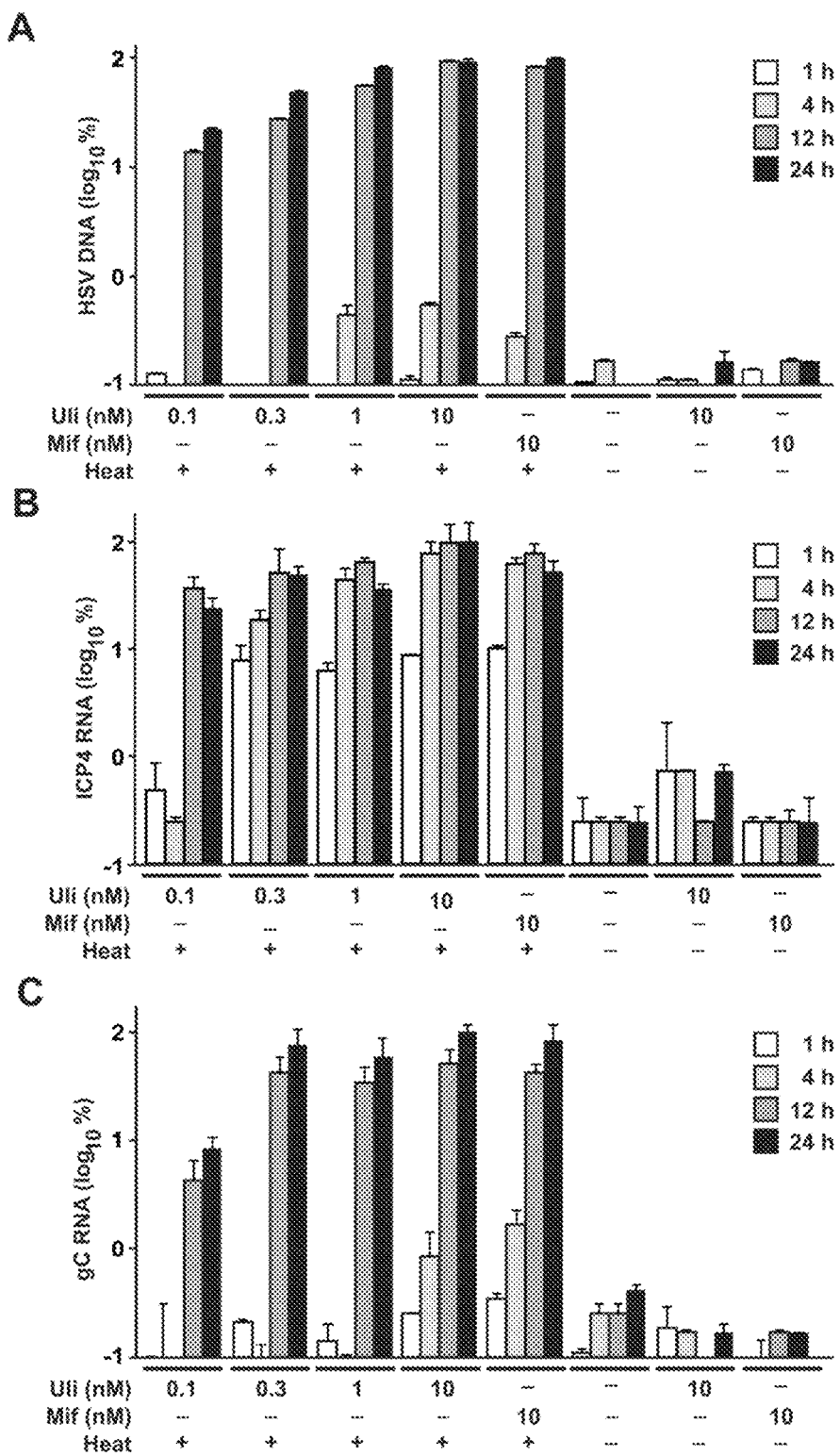
FIG. 5 relates to regulation of viral DNA replication and transcription in Vero cells infected with HSV-GS3. Multiple infected cultures were subjected to the treatments indicated in the panels. Heat treatment (43.5° C. for 30 min) was administered 4 h after infection, and sets of cultures were harvested 1, 4, 12 and 24 h later, and DNA and RNA were extracted and analyzed by qPCR and RT-qPCR, respectively. Uli: ulipristal. (A) HSV DNA. (B) ICP4 RNA. (C) gC RNA. Values and standard deviations were normalized relative to the highest value in each panel.

Results obtained are shown in FIG. 5. FIG. 5A shows that viral DNA replication depended both on heat treatment and small-molecule regulator. For ulipristal it was demonstrated that DNA replication was dependent on regulator dose. Compatible data were obtained for the expression of the ICP4 genes (regulated genes) and the late gC gene (not subject to deliberate regulation) (FIGS. 5B & C).

Example 3: Apparent Inability of a Replication-Competent Controlled Virus to Replicate In Vivo in the Absence of Deliberate Activation The goal of this experiment was to demonstrate that, in the absence of heat and small-molecule regulator, the GS vectors are as tightly "off" in mice as they appear to be in cell culture. Four to six week old out-bred ND4 Swiss Webster female mice (Harlan Sprague-Dawley, Inc.) were infected with similar amounts of HSV-GS1 or 17syn+ wild type virus on the lightly abraded plantar surface of both rear feet following saline pre-treatment. At 4, 8, and 21 days post infection, 4 mice per time point were euthanized and the feet and dorsal root ganglia (DRG) were harvested, homogenized in TRIzol, and DNA and RNA extracted. DNA was subjected to Taqman Realtime PCR for quantitative analysis for HSV-1 DNA; RNA was analyzed following RT by Taqman Realtime PCR for the presence of ICP4 and glycoprotein C (gC) transcripts as previously described. Kubat, N.J. et al. 2004. The herpes simplex virus type 1 latency-associated transcript (LAT) enhancer/rcr is hyperacetylated during latency independently of LAT transcription. J. Virol. 78: 12508-18. The real-time primer/probe sequences are disclosed in Table 3.

Results showed a complete absence of HSV-GS1 gene expression in feet as well as in DRG (Table 4). Consistent with this result implying that HSV-GS1 was incapable of replication was the finding that DNA amounts of HSV-GS1 were orders of magnitude lower than those of wild-type virus HSV 17syn+. Replication efficiency difference at 8 days was 151 fold in feet and 200 fold in DRG, respectively.

TABLE 4

HSV-GS1 and wild type HSV-1: replication and viral gene expression

| Time post infection | HSV 17+ | | | HSV-GS1 | | |
|---|---|---|---|---|---|---|
| | DNA | RNA ICP4 | RNA gC | DNA | RNA ICP4 | RNA gC |
| Feet: | | | | | | |
| 4 | 49,500 | 1,290 | 5,742 | 1,222 | ND | ND |
| 8 | 35,773 | 976 | 5,332 | 237 | ND | ND |
| 21 | 49 | ND* | ND | ND | ND | ND |
| DRG: | | | | | | |
| 4 | 12,674 | 576 | 3,563 | 59 | ND | ND |
| 8 | 14,986 | 877 | 9,230 | 75 | ND | ND |
| 21 | 5,754 | ND* | ND | 45 | ND | ND |

*ND = below the limit of detection.

Example 4: Activation In Vivo of a Replication-Competent Controlled Virus of the Invention In these experiments, virus replication in a mouse model was estimated by the biochemical methods of quantification of viral DNA and expression of viral genes. DNA amounts and viral transcript amounts were measured at both the foot (site of virus inoculation) and in the dorsal root ganglia (DRG) (site of HSV acute replication and latency). One such experiment had the design summarized in Table 5. This experiment was also aimed at determining the lowest effective in vivo dose of ulipristal.

TABLE 5

| Treatment groups | | | |
|---|---|---|---|
| | Ulipristal | | No drug |
| | 1 µg/kg | 5 µg/kg | 50 µg/kg | — |
| Heat treatment | X | X | X | X |
| No heat treatment | | X | | |

Outbred Swiss-webster female mice (4-6 weeks old) were inoculated with 1×10⁵ pfu of HSV-GS3 vector following saline-pretreatment and light abrasion of both rear footpads. Each treatment group consisted of 5 mice. Drug treatment (ulipristal) was administered IP at the time of infection. Heat treatment was performed at 45° C. for 10 min (by immersion of hind feet in a waterbath) 3 h after virus administration. Mice were allowed to recover at 37° C. for 15 min. Mice were sacrificed 24 hours post heat induction, and the feet and DRG were dissected and snap-frozen in RNA/ater (Sigma-Aldrich). DNA and RNA were extracted by grinding the tissues in TRIzol (Life Technologies), and back-extracting the DNA from the interface. DNA was subjected to Taqman Realtime PCR for quantitative analysis for HSV-1 DNA. RNA was analyzed following reverse transcription (RT) by Taqman PCR for the presence of ICP4 and glycoprotein C (gC) transcripts. DNA and RNA quantities were normalized relative to the cellular gene APRT.

Figure 6:
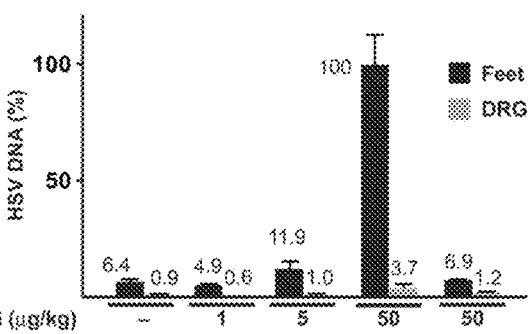
FIG. 6 relates to regulation of HSV-GS3 DNA replication and transcription, and comparison of replicative yields between HSV-GS3 and KD6 in the mouse footpad model. Adult outbred mice were inoculated on the slightly abraded footpads of their hind legs with $1\times10^5$ PFU of HSV-GS3 or KD6. Indicated doses of ulipristal were administered intraperitoneally at the time of infection. Localized heat treatment at 45° C. for 10 min was performed 3 h after virus administration. Mice were sacrificed 24 h (panels A-C) or 4 days (panel D) post heat treatment, and DNA and RNA were isolated from feet and dorsal root ganglia (DRG) and analyzed by qPCR and RT-qPCR, respectively. (A) HSV DNA. (B) ICP4 RNA. (C) gC RNA. (D) HSV DNA at 4 days post heat treatment. Values and standard deviations were normalized relative to the highest value in each panel. ND: none detected.
Figure 6:
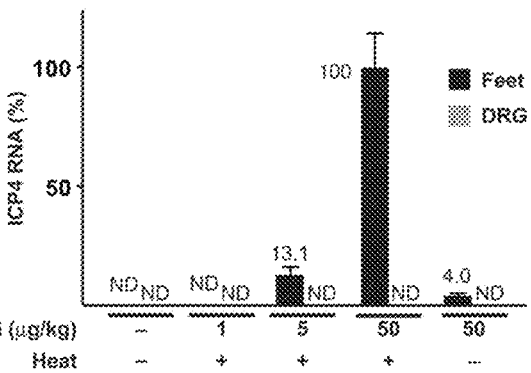
Figure 6:
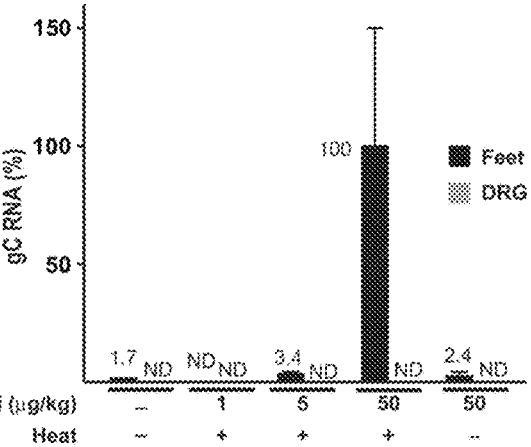
Figure 6:
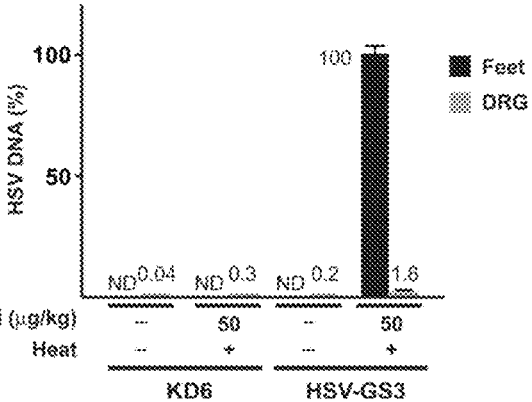

Results are shown in FIG. 6. FIG. 6A shows that replication in the feet depended both on heat treatment and small-molecule regulator. Furthermore, DNA replication was dependent on regulator dose. Compatible data were obtained for the expression of ICP4 genes (regulated genes) and the late gC gene (not subject to deliberate regulation) (FIGS. 6B & C). Small-molecule regulator alone (in the absence of a heat treatment) did essentially not stimulate DNA replication and at most marginally increased expression of ICP4 and gC transcripts.

Replicative yields of HSV-GS3 and replication-defective virus KD6 (ICP4-) were compared in the experiment shown in FIG. 6D. This experiment was performed as the previous experiment with the exception that mice were sacrificed 24 hours post heat induction. Results showed that viral DNA could essentially only be detected in samples from the feet of HSV-GS3-infected animals that had received heat treatment and ulipristal. Very little DNA was found in DRG, and essentially none in KD-6-infected animals or in not-activated HSV-GS3-infected animals.

Example 5: Immunization/Challenge Experiment Comparing a Replication-Competent Controlled Virus of the Invention with a Replication-Defective Comparison Virus (KD6)

The goal of this type of experiment was to demonstrate that immunizing mice with the HSV-GS3 virus under inducing conditions elicits a strong protective immune response against subsequent challenge with a lethal dose of wild-type HSV-1.

(a) Survival

Experimental Design:

TABLE 6

| | Immunization treatment groups | | | |
|---|---|---|---|---|
| Group | Mock | KD6 | HSV-GS3 | HSV-GS3 (induced) |
| Immunization Tx* | vehicle (MEM + 10% FBS) | 50,000 pfu of KD6 (non-replicating, ICP4-negative HSV-1) | 50,000 pfu of HSV-GS3 | 50,000 pfu of HSV-GS3 |
| Challenge Tx | 10,000 pfu of HSV-1 strain 17syn+ | 10,000 pfu of HSV-1 strain 17syn+ | 10,000 pfu of HSV-1 strain 17syn+ | 10,000 pfu of HSV-1 strain 17syn+ |

*All Tx were in a volume of 0.050 ml/mouse.

a) Immunization:

Mice were initially immunized in the experimental groups shown in Table 6. Each group contained 20 mice (ND4 Swiss Webster females, 4-6 weeks). Each vector was applied to the lightly abraded plantar surface of both rear feet following saline pre-treatment.

b) Induction:

The HSV-GS3 vector was induced in the "HSV-GS3 (induced)" group as follows: mifepristone (0.5 mg/kg) was administered i.p. at the time of immunization and again 24 h later. Heat was applied 3 h post immunization by immersing both rear feet in a 43.5° C. water bath for 30 min. Following immersion, the hind limbs were dried off, and the mice kept warm with a heat lamp until dry and warm.

c) Challenge:

22 days post immunization the mice were challenged with a 20-fold lethal dose of wild type HSV-1 strain 17syn+ applied to the lightly abraded plantar surface of both rear feet following saline pre-treatment. Efficacy of each immunization treatment was then assessed by a modified endpoint assay. Note that the modified endpoint assay involved euthanizing mice that were considered moribund (will not survive) based on clinical assessment (mice showing signs of bilateral hindlimb paralysis and CNS involvement, convulsions, and unable to move on their own to take food or water).

Results:

Mice in the mock treatment group began to show signs of hindlimb paralysis and CNS infection as early as 6 days post challenge, while all three immunization groups appeared completely healthy until 8-9 days post challenge. Table 7 depicts the number of mice surviving at the end of the experiment (mice were followed 30 d post challenge). The results demonstrate that, while all treatments were able to protect at least some mice against a 20 fold lethal challenge of HSV-1, only the induced HSV-GS3 virus treatment was able to afford substantial protection in the mice.

TABLE 7

Results of immunization/challenge experiment

| Group | No. of survivors (from groups of 20 animals) |
| --- | --- |
| HSV-GS3 Induced | 14 |
| KD6 | 5 |
| HSV-GS3 | 3 |
| Mock | 0 |

A further experiment is presented below.

Experimental Design a) Immunization:
Mice were initially immunized in the experimental groups shown in Table 6. Each group contained 10 mice (ND4 Swiss Webster females, 4-6 weeks). Each vector was applied to the lightly abraded plantar surface of both rear feet following saline pre-treatment.
b) Induction:
The HSV-GS3 vector was induced in the "HSV-GS3 (induced 2 times)" group as follows: ulipristal (50 µg/kg) was administered i.p. at the time of immunization. Heat was applied 3 h post immunization by immersing both rear feet in a 45° C. water bath for 10 min. Following immersion, the hind limbs were dried off, and the mice kept warm with a heat lamp until dry and warm. The latter activation procedure was repeated 24 h later.
c) Challenge:
approximately three weeks post immunization the mice were challenged with a 2-fold lethal dose of wild type HSV-1 strain 17syn+ applied to the lightly abraded plantar surface of both rear feet following saline pre-treatment. Efficacy of each immunization treatment was then assessed by a modified endpoint assay. Note that the modified endpoint assay involved euthanizing mice that were considered moribund (will not survive) based on clinical assessment (mice showing signs of bilateral hindlimb paralysis and CNS involvement, convulsions, and unable to move on their own to take food or water).

Results:
Table 9 depicts the number of mice surviving at the end of the experiment (mice were followed 30 d post challenge). The results demonstrate that, while all treatments were able to protect at least some mice against a 2 fold lethal challenge of HSV-1, only the induced HSV-GS3 virus treatment was able to afford substantial protection in the mice.

TABLE 9

Results of immunization/challenge experiment

| Group | No. of survivors (from groups of 10 animals) |
| --- | --- |
| HSV-GS3 Induced 2 times | 8 |
| KD6 | 4 |
| HSV-GS3 | 3 |
| Mock | 2 |

(b) Replication of Challenge Virus

Experimental Design:
a) Immunization:
Mice were immunized as shown in Table 6. Each group contained 5 mice (ND4 Swiss females, 4-6 weeks). Each vector was applied to the lightly abraded plantar surface of the both rear feet following saline pre-treatment.
b) Induction:
The HSV-GS3 vector was induced in the "HSV-GS3 (induced)" group as follows: mifepristone (0.5 mg/kg) was administered i.p. at the time of immunization and again 24 h later. Heat was applied 3 h post immunization by immersing both rear hind feet in a 43.5° C. waterbath for 30 min. Following immersion, the hindlimbs were dried off, and the mice kept warm with a heat lamp until dry and warm.
c) Challenge:
22 days post immunization the mice were challenged with a 20-fold lethal dose of wild type HSV-1 strain 17syn+ applied to the lightly abraded plantar surface of the both rear feet following saline pre-treatment. Four days post challenge the mice were euthanized and feet were dissected and homogenized. The tissue homogenates were then diluted and titrated on rabbit skin cells (RS) for infectious (17syn+) virus.

Results:
Table 10 depicts the results of the titration data. These results illustrate that, while all of the immunization treatments were able to reduce replication to some extent (relative to mock) in the feet following challenge with HSV-1, HSV-GS3 (induced) mice showed by far the lowest challenge virus titer at four days post challenge (about two orders of magnitude lower than mock).

TABLE 8

Immunization treatment groups

| Group | Mock | KD6 | HSV-GS3 | HSV-GS3 induced 2 times |
| --- | --- | --- | --- | --- |
| Vaccination Tx* | vehicle (MEM + 10% FBS) | 50,000 pfu of KD6 (non-replicating ICP4-HSV-1) | 50,000 pfu of HSV-GS3 | 50,000 pfu of HSV-GS3 |
| Challenge Tx | 1,000 pfu of HSV-1 strain 17syn+ | 1,000 pfu of HSV-1 strain 17syn+ | 1,000 pfu of HSV-1 strain 17syn+ | 1,000 pfu of HSV-1 strain 17syn+ |

*All Tx were in a volume of 0.050 ml/mouse.

TABLE 10

Infectious virus (pfu) detected in the feet of mice, 4 d post challenge

| Mock | KD6 | HSV-GS3 | HSV-GS3 (induced) |
|---|---|---|---|
| $5.5 \times 10^5$ +/− $1.2 \times 10^4$ | $4.0 \times 10^4$ +/− $8.3 \times 10^2$ | $9.4 \times 10^4$ +/− $3.1 \times 10^4$ | $6.2 \times 10^3$ +/− $1.5 \times 10^2$ |

Example 6: Adenovirus Vectors that Co-Replicate with Replication-Competent Controlled Virus (a) Adenovirus Having a Replication-Essential Gene that is Activated by the Transactivator of a Replication-Competent Controlled Virus rAd3 lacks nucleotides 28,130-30,820 encompassing E3. Nucleotide numbers relating to the adenovirus type 5 genome are as defined in GI: 33694637. Davison et al. 2003. J. Gen. Virol. 84, 2895-2908. Further, it contains a complete E1 gene that is functionally linked to a GAL4 site-containing minimal promoter.

The simplified system for generating recombinant adenovirus developed by He et al. (Proc. Natl. Acad. Sci. USA 95: 2509-2514 (1998)) is employed to construct rAd3. This system has been made available commercially by Stratagene Corp. of La Jolla, Calif. A manual entitled "AdEasy™ Adenoviral Vector System" (revision no. 060002) is distributed by the Company to its customers and is also available at the Company's website.

Mutagenesis is carried out in transfer vector pShuttle (He et al. (1998)) distributed by Statagene Corporation. For the complete nucleotide sequence of this plasmid see FIG. 7 of U.S. Pat. No. 7,906,312. According to Stratagene's manual entitled "AdEasy™ Adenoviral Vector System" (revision no. 060002), pShuttle contains the following adenovirus sequence elements: left inverted terminal repeat, encapsidation signal (Ad 1-331), "right arm homology region" (3,534-5790), "left arm homology region" (34,931-35,935) and right inverted terminal repeat.

The right arm homology region of pShuttle is replaced with Ad sequences also containing the beginning of the E1 region in addition to the homology region. First, pShuttle DNA is digested with NotI and PmeI, and the vector fragment gel-purified. Next, a fragment containing Ad 496-5780 is obtained by PCR amplification from plasmid pXC1 (Microbix Corporation, Toronto, ON). The nucleotide sequence of this plasmid is presented, e.g., in FIG. 9 of U.S. Pat. No. 7,906,312. The latter PCR amplification is carried out using a forward primer (reading into the E1 gene) containing a SbfI restriction site and a reverse primer containing a PmeI restriction site. The resulting PCR fragment is digested with SbfI and PmeI. Furthermore, a DNA fragment encompassing nucleotides 4634 to 323 of plasmid pGene/V5-His (Invitrogen Corporation of Carlsbad, Calif.) is PCR-amplified using an appropriate forward primer containing a NotI restriction site and a reverse primer containing a SbfI restriction site. The PCR-amplified fragment is digested with NotI and SbfI. The latter two end-digested PCR fragments are ligated to the pShuttle vector fragment. A plasmid containing the latter three fragments as evidenced by restriction analysis is termed pShuttle-E1-GAL4.

To prepare recombinant Ad, pShuttle-E1-GAL4 DNA is linearized by PmeI digestion and co-electroporated with pAdEasy-1 DNA (He et al. 1998) into E. coli BJ5183 cells. BJ5183 cells (Stratagene catalog no. 200154) have the cellular components necessary to carry out homologous recombination between introduced viral sequences. Detailed methods for the generation of recombinant Ad plasmids and the subsequent production of recombinant Ad viruses are discussed in He et al. (1998) and in Stratagene manual "AdEasy™ Adenoviral Vector System" (revision no. 060002). Briefly, recombinant Ad plasmids are characterized by restriction digestion. After preparation of a sufficient amount of DNA of a correct recombinant, the DNA is digested with PacI to separate plasmid sequences and inserted sequences comprising the Ad sequences. To produce recombinant Ad virus, the digested DNA is transfected into 293 cells. Using standard technology (briefly described in He et al. (1998); see also Graham and Prevec. 1991. Manipulation of adenovirus vectors. In: Methods in Molecular Biology, Gene Transfer and Expression Protocols, vol. 7, ed. Murray, The Humana Press Inc., Clifton, N.J., pp. 109-127), virus plaques are isolated, and rAd3 stocks prepared. Viral stocks can be purified by CsCl gradient centrifugation or chromatographic procedures.

In mammalian cells such as human fibroblasts co-infected with rAd3 and HSV-GS3 viruses, administration of an appropriate heat dose in the presence of an effective concentration of small molecule regulator, e.g., mifepristone or ulipristal, results in activation of replication of both viruses.

(b) Adenovirus Lacking a Replication-Essential Gene Complemented by a HSV-GS Virus that Conditionally Expresses the Ad Replication-Essential Gene An E1A-defective Ad5 (rAd4) is prepared as follows: the right arm homology region of pShuttle is replaced with a longer Ad E1 sequence. First, pShuttle DNA is digested with NotI and PmeI, and the vector fragment gel-purified. Next, a fragment containing Ad 496-5780 is obtained by PCR amplification from plasmid pXC1 (Microbix Corporation, Toronto, ON). The latter PCR amplification is carried out using a forward primer (reading into the E1 gene) containing a NotI restriction site and a reverse primer containing a PmeI restriction site. The resulting PCR fragment is digested with NotI and PmeI. The latter end-digested PCR fragment is ligated to the pShuttle vector fragment. A plasmid containing the latter three fragments as evidenced by restriction analysis is termed pShuttle-E1.

To prepare recombinant Ad, pShuttle-E1 DNA is linearized by PmeI digestion and co-electroporated with pAdEasy-1 into E. coli BJ5183 cells. Recombinant Ad plasmids are characterized by restriction digestion. After preparation of a sufficient amount of DNA of a correct recombinant, the DNA is digested with PacI to separate plasmid sequences and inserted sequences comprising the Ad sequences. To produce recombinant Ad, the digested DNA is transfected into 293 cells. Using standard technology, virus plaques are isolated, and rAd4 stocks prepared. Viral stocks can be purified by CsCl gradient centrifugation or chromatographic procedures.

To prepare HSV-GS7, the GAL4 promoter-E1 region from plasmid pShuttle-E1-GAL4 is PCR-amplified using two of the same primers that have been used in the construction of the latter plasmid: as forward primer is used the same forward primer that has been employed to amplify the pGene/V5-His promoter fragment, and as reverse primer is used the same reverse primer that has been employed to amplify the E1 fragment from pXC1. (The primers are phosphorylated.) The PCR fragment is gel-purified. For the vector, pBS-KS:UL37/38 is digested with BspE1 and AflII, and the resulting 3,772 bp fragment is treated with T4 DNA polymerase, gel-purified and SAP-treated, and then ligated to the above PCR fragment. Following transformation, colonies are screened by restriction digestion, and one colony is expanded that contains a plasmid with the correct insertion as verified by restriction enzyme analysis and then by sequence analysis. This plasmid is termed pUL37/38:GAL4-E1.

One μg of pUL37/38:GAL4-E1 is co-transfected with 10 μg of purified HSV-GS3 virion DNA into E5 cells by calcium phosphate precipitation. Subsequent to the addition of mifepristone to the medium, the transfected cells are exposed to 43.5° C. for 30 minutes and then incubated at 37° C. Subsequently on days 2 and 3, the cells are again incubated at 43.5° C. for 30 minutes and then returned to 37° C. Plaques are picked and amplified on 96 well plates of E5 cells in media supplemented with mifepristone. The plates are incubated at 43.5° C. for 30 minutes 1 hour after infection and then incubated at 37° C. Subsequently on days 2 and 3, the plates are also shifted to 43.5° C. for 30 minutes and then returned to 37° C. After the wells showed 90-100% CPE, the plates are dot-blotted and the dot-blot membrane hybridized with a $^{32}$P-labeled oligonucleotide probe to the adenovirus E1 region. A positive well is re-plaqued and re-probed several times and verified by sequence analysis to contain the expected GAL4-Ad5 E1 gene sequence. This recombinant is designated HSV-GS7.

In mammalian cells such as human fibroblasts co-infected with rAd4 and HSV-GS7 viruses, administration of an appropriate heat dose in the presence of an effective concentration of small molecule regulator, e.g., mifepristone or ulipristal, results in activation of replication of both viruses.

All references cited in this application, including publications, patents and patent applications, shall be considered as having been incorporated in their entirety.

The invention claimed is:

1. A method of immunizing a mammalian subject comprising (a) administering to an inoculation site region in the body of a mammalian subject a composition comprising an effective amount of a replication-competent controlled herpesvirus which is a recombinant virus in which one or more replication-essential genes have been placed under the control of a gene switch that is inserted in the genome of the recombinant virus and that can be activated deliberately, and (b) exposing the inoculation site region of the mammalian subject to a localized activation treatment that activates the recombinant virus to undergo a round of replication in the inoculation site region and induces a functional immune response, wherein the inoculation site region is a cutaneous region, a subcutaneous region, or a mucosal membrane and the localized activation treatment comprises a heat treatment.

2. The method according to claim 1, wherein the replication-competent controlled herpesvirus is a recombinant virus selected from the group consisting of an HSV-1, an HSV-2, a varicella zoster virus, a cytomegalovirus and a roseola virus.

3. The method according to claim 1, wherein the replication-competent controlled herpesvirus is a recombinant herpesvirus that comprises an inserted gene encoding a small-molecule regulator-activated transactivator which gene is functionally linked to a nucleic acid sequence that acts as a heat shock promoter or to a nucleic acid sequence that acts as a heat shock promoter as well as a transactivator-responsive promoter, and one or more transactivator-responsive promoters that are functionally linked to the one or more replication-essential genes.

4. The method according to claim 3, wherein the replication-competent controlled herpesvirus further comprises at least one gene from another pathogen, a heterologous gene encoding an immune-modulatory polypeptide and a heterologous gene encoding another polypeptide.

5. The method according to claim 1, wherein the replication-competent controlled herpesvirus comprises a gene that encodes an HIV envelope protein antigen or an HIV internal protein antigen.

6. The method according to claim 3, wherein the replication-competent controlled herpesvirus is a recombinant virus selected from the group consisting of an HSV-1, an HSV-2, a varicella zoster virus, a cytomegalovirus and a roseola virus.

7. The method according to claim 3, wherein the replication-competent controlled herpesvirus is a recombinant HSV-1 or HSV-2 and the replication-essential viral genes that are functionally linked to transactivator-responsive promoters include at least all copies of the ICP4 gene or the ICP8 gene.

8. The method according to claim 3, wherein the small-molecule regulator-activated transactivator contains a truncated ligand-binding domain from a progesterone receptor and is activated by a progesterone receptor antagonist or other molecule capable of interacting with the ligand-binding domain and activating the transactivator.

9. The method according to claim 1, wherein the replication-competent controlled herpesvirus is a recombinant HSV-1 selected from the group consisting of HSV-GS1, HSV-GS3, HSV-GS4 and HSV-GS6, wherein the recombinant HSV-1 further comprises at least one gene from another pathogen, a heterologous gene encoding an immune-modulatory polypeptide and a heterologous gene encoding another polypeptide.

10. The method according to claim 3, further comprising administering a second virus that has a host range that overlaps that of the replication-competent controlled herpesvirus, the second virus having a replication-essential gene functionally linked to a transactivator-responsive promoter.

11. The method according to claim 3, further comprising a second virus that has a host range that overlaps that of the replication-competent controlled herpesvirus, wherein a replication-essential gene from the second virus is expressed under the control of a transactivator-responsive promoter by the replication-competent controlled herpesvirus and the second virus is defective in said replication-essential gene.

12. The method according to claim 3, wherein the composition that is administered to the inoculation site region further comprises an effective amount of a small-molecule regulator that is capable of activating the transactivator.

13. The method according to claim 3, wherein:

(a) the composition comprising an effective amount of the replication-competent controlled herpesvirus is administered to the inoculation site region, and (b) the inoculation site region is exposed to an activating heat dose in the presence in the inoculation site region of an effective concentration of a small-molecule regulator that activates the transactivator of the replication-competent controlled herpesvirus.

14. The method according to claim 12, wherein:

(a) the composition further comprising an effective amount of a small-molecule regulator is administered to the inoculation site region, and (b) the inoculation site region is exposed to an activating heat dose.

15. The method according to claim 1, wherein the replication-competent controlled herpesvirus is a recombinant herpesvirus that comprises an inserted gene encoding a transactivator activated by a small-molecule regulator, wherein the gene encoding the transactivator is functionally linked to a nucleic acid that acts as a heat shock promoter, and one or more transactivator-responsive promoters that are functionally linked to one or more replication-essential genes.

16. The method according to claim 15, wherein the replication-competent controlled herpesvirus further comprises at least one gene from another pathogen, a heterologous gene encoding an immune-modulatory polypeptide and a heterologous gene encoding another polypeptide.

17. The method according to claim 1, wherein the replication-competent controlled herpesvirus is a recombinant herpesvirus that comprises an inserted gene encoding a small-molecule regulator-activated transactivator wherein the gene encoding the transactivator is functionally linked to a nucleic acid that acts as a constitutively active promoter or a transactivator-responsive promoter, a first replication-essential gene of the replication-competent controlled herpesvirus is functionally linked to a promoter activated by heat and a second replication-essential gene of the replication-competent controlled herpesvirus is functionally linked to a transactivator-responsive promoter.

18. The method according to claim 17, wherein the replication-competent controlled herpesvirus further comprises at least one gene from another pathogen, a heterologous gene encoding an immune-modulatory polypeptide and a heterologous gene encoding another polypeptide.

19. The method according to claim 1, wherein the replication-competent controlled herpesvirus is a recombinant HSV-1 selected from the group consisting of HSV-GS1, HSV-GS3, HSV-GS4 and HSV-GS6.

* * * * *

SEQUENCE LISTING

```
<160> NUMBER OF SEQ ID NOS: 22

<210> SEQ ID NO 1
<211> LENGTH: 21
<212> TYPE: DNA
<213> ORGANISM: Homo sapiens

<400> SEQUENCE: 1
tcgacaactc cgagtttcag c                                            21

<210> SEQ ID NO 2
<211> LENGTH: 39
<212> TYPE: DNA
<213> ORGANISM: Homo sapiens

<400> SEQUENCE: 2
ctcctcgcgg ccgcatcgat ccatagagcc caccgcatc                         39

<210> SEQ ID NO 3
<211> LENGTH: 42
<212> TYPE: DNA
<213> ORGANISM: herpes simplex virus 1

<400> SEQUENCE: 3
ctcctcaagc ttctcgagca cacggagcgc ggctgccgac ac                     42

<210> SEQ ID NO 4
<211> LENGTH: 35
<212> TYPE: DNA
<213> ORGANISM: Herpes simplex virus 1

<400> SEQUENCE: 4
ctcctcggta ccccatggag gccagcagag ccagc                             35

<210> SEQ ID NO 5
<211> LENGTH: 42
<212> TYPE: DNA
<213> ORGANISM: Herpes simplex virus 1

<400> SEQUENCE: 5
ctcctcgcgg ccgcactagt tccgcgtgtc cctttccgat gc                     42

<210> SEQ ID NO 6
<211> LENGTH: 58
<212> TYPE: DNA
<213> ORGANISM: Herpes simplex virus 1

<400> SEQUENCE: 6
```

```
ctcctcctcg agaagcttat gcatgagctc gacgtctcgg cggtaatgag atacgagc     58
```

<210> SEQ ID NO 7
<211> LENGTH: 32
<212> TYPE: DNA
<213> ORGANISM: Herpes simplex virus 1

<400> SEQUENCE: 7

```
ctcctcagaa cccaggacca gggccacgtt gg                                 32
```

<210> SEQ ID NO 8
<211> LENGTH: 33
<212> TYPE: DNA
<213> ORGANISM: Herpes simplex virus 1

<400> SEQUENCE: 8

```
ctcctcatgg agacaaagcc caagacggca acc                                33
```

<210> SEQ ID NO 9
<211> LENGTH: 36
<212> TYPE: DNA
<213> ORGANISM: Herpes simplex virus 1

<400> SEQUENCE: 9

```
ctcctcggag accggggttg gggaatgaat ccctcc                             36
```

<210> SEQ ID NO 10
<211> LENGTH: 35
<212> TYPE: DNA
<213> ORGANISM: Herpes simplex virus 1

<400> SEQUENCE: 10

```
ctcctcgcgg ggcgtgggag gggctggggc ggacc                              35
```

<210> SEQ ID NO 11
<211> LENGTH: 22
<212> TYPE: DNA
<213> ORGANISM: Herpes simplex virus 1

<400> SEQUENCE: 11

```
agagggacat ccaggacttt gt                                            22
```

<210> SEQ ID NO 12
<211> LENGTH: 19
<212> TYPE: DNA
<213> ORGANISM: Herpes simplex virus 1

<400> SEQUENCE: 12

```
caggcgcttg ttggtgtac                                                19
```

<210> SEQ ID NO 13
<211> LENGTH: 16
<212> TYPE: DNA
<213> ORGANISM: Herpes simplex virus 1

<400> SEQUENCE: 13

```
accgccgaac tgagca                                                   16
```

<210> SEQ ID NO 14
<211> LENGTH: 15
<212> TYPE: DNA
<213> ORGANISM: Herpes simplex virus 1

<400> SEQUENCE: 14
cacgggccgc ttcac                                                    15

<210> SEQ ID NO 15
<211> LENGTH: 17
<212> TYPE: DNA
<213> ORGANISM: Herpes simplex virus 1

<400> SEQUENCE: 15
gcgatagcgc gcgtaga                                                  17

<210> SEQ ID NO 16
<211> LENGTH: 14
<212> TYPE: DNA
<213> ORGANISM: Herpes simplex virus 1

<400> SEQUENCE: 16
ccgacgcgac ctcc                                                     14

<210> SEQ ID NO 17
<211> LENGTH: 17
<212> TYPE: DNA
<213> ORGANISM: Herpes simplex virus 1

<400> SEQUENCE: 17
cctccacgcc caaaagc                                                  17

<210> SEQ ID NO 18
<211> LENGTH: 22
<212> TYPE: DNA
<213> ORGANISM: Herpes simplex virus 1

<400> SEQUENCE: 18
ggtggtgttg ttcttgggtt tg                                            22

<210> SEQ ID NO 19
<211> LENGTH: 15
<212> TYPE: DNA
<213> ORGANISM: Herpes simplex virus 1

<400> SEQUENCE: 19
ccccacgtcc acccc                                                    15

<210> SEQ ID NO 20
<211> LENGTH: 25
<212> TYPE: DNA
<213> ORGANISM: mus musculus

<400> SEQUENCE: 20
ctcaagaaat ctaaccctg actca                                          25

<210> SEQ ID NO 21
<211> LENGTH: 16
<212> TYPE: DNA
<213> ORGANISM: Mus musculus

```
<400> SEQUENCE: 21
gcgggacagg ctgaga                                                        16

<210> SEQ ID NO 22
<211> LENGTH: 15
<212> TYPE: DNA
<213> ORGANISM: Mus musculus

<400> SEQUENCE: 22
ccccacacac acctc                                                         15
```